(12) United States Patent
Albert et al.

(10) Patent No.: US 10,723,687 B2
(45) Date of Patent: *Jul. 28, 2020

(54) METHODS OF MAKING ACRYLIC ACID FROM LACTIC ACID OR ITS DERIVATIVES IN LIQUID PHASE

(71) Applicant: The Procter & Gamble Company, Cincinnati, OH (US)

(72) Inventors: Jakob Albert, Erlangen (DE); Peter Wasserscheid, Erlangen (DE); Nicola Taccardi, Erlangen (DE); Jens Nagengast, Erlangen (DE); Matthias Kehrer, Erlangen (DE); Julian Kadar, Erlangen (DE); Dimitris Ioannis Collias, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/867,975

(22) Filed: Jan. 11, 2018

(65) Prior Publication Data

US 2018/0148400 A1 May 31, 2018

Related U.S. Application Data

(63) Continuation-in-part of application No. 15/661,012, filed on Jul. 27, 2017.

(60) Provisional application No. 62/522,190, filed on Jun. 20, 2017, provisional application No. 62/490,079, filed on Apr. 26, 2017, provisional application No. 62/427,298, filed on Nov. 29, 2016, provisional application No. 62/384,773, filed on Sep. 8, 2016, provisional application No. 62/368,213, filed on Jul. 29, 2016.

(51) Int. Cl.
| | | |
|---|---|---|
| *C07C 51/377* | (2006.01) | |
| *C07C 57/04* | (2006.01) | |
| *C07C 59/315* | (2006.01) | |
| *C07C 59/08* | (2006.01) | |
| *C07C 51/09* | (2006.01) | |

(52) U.S. Cl.
CPC ............ *C07C 51/377* (2013.01); *C07C 51/09* (2013.01); *C07C 57/04* (2013.01); *C07C 59/08* (2013.01); *C07C 59/315* (2013.01); *C07C 2531/24* (2013.01)

(58) Field of Classification Search
CPC ....... C07C 51/09; C07C 51/377; C07C 57/04; C07C 59/08; C07C 59/315; C07C 2531/24; C07C 51/347; C07C 67/327; B01J 27/122; B01J 27/125; B01J 27/138; B01J 27/16; B01J 31/0279; B01J 31/0281; B01J 31/0288; B01J 31/0298; B01J 31/26; B01J 27/08; B01J 31/0277; B01J 31/30; G01N 2333/47; G01N 2333/4704; G01N 33/4833; G01N 33/57484; G01N 33/6848

See application file for complete search history.

(56) References Cited

U.S. PATENT DOCUMENTS

| | | |
|---|---|---|
| 9,309,180 B2 | 4/2016 | Kuppinger et al. |
| 10,106,484 B2 | 10/2018 | Velasquez |
| 2010/0152077 A1 | 6/2010 | Allston et al. |
| 2012/0004449 A1 | 1/2012 | Bhattacharyya et al. |
| 2015/0105584 A1* | 4/2015 | Velasquez ............ B01J 37/0036 562/579 |
| 2017/0370895 A1 | 12/2017 | Han et al. |
| 2018/0029026 A1 | 2/2018 | Albert et al. |
| 2018/0029969 A1 | 2/2018 | Albert et al. |
| 2018/0133705 A1 | 5/2018 | Albert et al. |
| 2018/0148400 A1 | 5/2018 | Albert et al. |
| 2018/0370895 A1 | 12/2018 | Verkuijl et al. |

FOREIGN PATENT DOCUMENTS

| | | | |
|---|---|---|---|
| EP | 15201469.2 | * 12/2015 | |
| EP | 2977380 A1 | 1/2016 | |
| KR | 101034050 | * 5/2011 | |
| WO | WO2014172540 | * 10/2014 | |
| WO | WO2014172540 A2 | 10/2014 | |
| WO | WO201557904 A1 | 4/2015 | |
| WO | WO-2017108890 A1 * | 6/2017 | ........... C07C 67/327 |

OTHER PUBLICATIONS

Dissociation Constants of Inorganic Acids and Bases, Published Nov. 2010 (Year: 2010).*
KR 101034050 translated (Year: 2011).*
U.S. Appl. No. 15/661,012, filed Jul. 27, 2017, Albert et al.
Search Report for PCT/US2017/044073 dated Nov. 8, 2017.
Terrade et al., "Catalytic Cracking of Lactide and Poly(Lactic Acid) to Acrylic Acid at Low Temperatures", ChemSusChem Communications, 2017, 10, pp. 1904-1908, DOI: 10.1002/cssc.201700108.
M. Ai, "Preparation of High-Surface-Area Titanium-Vanadium Binary Pyrophosphate Catalysts", Applied Catalysis, 1989, vol. 48, pp. 51-61.
E. Blanco et al., "Gas phase dehydration of lactic acid to acrylic acid over alkaline-earth phosphates catalysts", Catalysis Today, 2013, vol. 226, pp. 184-191.

* cited by examiner

*Primary Examiner* — Yevgeny Valenrod
*Assistant Examiner* — Blaine G Doletski
(74) *Attorney, Agent, or Firm* — James E Oehlenschlager

(57) ABSTRACT

Methods for making acrylic acid, acrylic acid derivatives, or mixtures thereof by contacting a feed stream containing lactic acid, lactic acid derivatives, or mixtures thereof with a molten salt catalyst comprising an ionic liquid (IL) and an acid in liquid phase are provided.

9 Claims, No Drawings

METHODS OF MAKING ACRYLIC ACID FROM LACTIC ACID OR ITS DERIVATIVES IN LIQUID PHASE

FIELD OF THE INVENTION

The present invention generally relates to methods of making acrylic acid, acrylic acid derivatives, or mixtures thereof. Specifically, the present invention relates to methods of making acrylic acid, acrylic acid derivatives, or mixtures thereof by contacting a feed stream containing lactic acid, lactic acid derivatives, or mixtures thereof with a molten salt catalyst in liquid phase.

BACKGROUND OF THE INVENTION

Acrylic acid, acrylic acid derivatives, or mixtures thereof are used today in a variety of industrial materials, such as adhesives, binders, coatings, paints, polishes, detergents, flocculants, dispersants, thixotropic agents, sequestrants, and superabsorbent polymers (SAP), which are used in disposable absorbent articles, including diapers and hygienic products. In terms of production process, acrylic acid is typically made today from the two-step catalytic oxidation of propylene, which in turn is produced from fossil resources, such as petroleum or natural gas. More on the oxidation of propylene to make acrylic acid and other production methods can be found in the Kirk-Othmer Encyclopedia of Chemical Technology, Vol. 1, pgs. 342-369 ($5^{th}$ Ed., John Wiley & Sons, Inc., 2004).

Fossil-derived acrylic acid uses resources that are not renewable as it takes hundreds of thousands of years to form naturally and only a short time to consume, and contributes to greenhouse emissions due to its high content of fossil-derived carbon. On the other hand, renewable resources refer to materials that are produced via a natural process at a rate comparable to their rate of consumption (e.g., within a 100-year time frame) and can be replenished naturally or via agricultural techniques. Examples of renewable resources include plants, such as sugar cane, sugar beets, corn, potatoes, citrus fruit, woody plants, lignocellulose, carbohydrate, hemicellulose, cellulosic waste, animals, fish, bacteria, fungi, and forestry products. As fossil resources become increasingly scarce, more expensive, and potentially subject to regulations for $CO_2$ emissions, there exists a growing need for non-fossil-derived acrylic acid, acrylic acid derivatives, or mixtures thereof that can serve as an alternative to fossil-derived acrylic acid, acrylic acid derivatives, or mixtures thereof.

Many attempts have been made over the last 80 years to make non-fossil-derived acrylic acid, acrylic acid derivatives, or mixtures thereof from renewable resources, such as lactic acid (also known as 2-hydroxypropionic acid) and other materials. From these resources, only lactic acid is produced today in high yield and purity from sugar (≥90% of theoretical yield, or equivalently, ≥0.9 g of lactic acid per g of sugar), and with economics which could support producing acrylic acid cost competitively to fossil-derived acrylic acid. As such, lactic acid or lactate presents a real opportunity of serving as a feedstock for bio-based acrylic acid, acrylic acid derivatives, or mixtures thereof.

The overwhelming majority of scientific literature and patent art describe the gas phase dehydration of lactic acid, lactic acid derivatives, or mixtures thereof to acrylic acid, acrylic acid derivatives, or mixtures thereof. However, liquid phase dehydration should offer significant advantages over the gas phase dehydration, for example, lower operating temperature and pressure, longer residence time, lower energy use and $CO_2$ emissions, wide selection of catalyst types (e.g. homogeneous and heterogeneous) and catalysts to choose from, lower coking potential of the catalysts, lower safety concerns, lower potential for lactic acid corrosion, wider selection of reactor designs, etc. U.S. Pat. No. 9,309,180 (assigned to Evonik Industries AG) discloses a process to dehydrate lactic acid and produce acrylic acid in liquid phase with the use of various metal salt catalysts, such as $K_2HPO_4$, $KH_2PO_4$, $BaHPO_4$, and mixtures of similar salts. At 300° C. and reaction time ranging from 4.4 h to 5.5 h, the yield of acrylic acid was between 0.1 mol % and 1.3 mol %.

Accordingly, there is a need for liquid phase dehydration methods of lactic acid, lactic acid derivatives, or mixtures thereof to acrylic acid, acrylic acid derivatives or mixtures thereof with high yield and selectivity.

SUMMARY OF THE INVENTION

In one embodiment of the present invention, a method of making acrylic acid, acrylic acid derivatives, or mixtures thereof is provided. The method comprises contacting a feed stream comprising lactic acid, lactic acid derivatives, or mixtures thereof with a molten salt catalyst in a reactor at a temperature; wherein said molten salt catalyst comprises an ionic liquid (IL) and an acid; and whereby acrylic acid, acrylic acid derivatives, or mixtures thereof are produced as a result of said contacting in said reactor.

In another embodiment of the present invention, a method of making acrylic acid, acrylic acid derivatives, or mixtures thereof is provided. The method comprises contacting a feed stream comprising 2-acetoxypropionic acid (2-APA) with a molten salt catalyst in a reactor at 220° C.; wherein said molten salt catalyst comprises tetrabutylphosphonium bromide ([$PBu_4$]Br) and pyrophosphoric acid ($H_4P_2O_7$) at a molar ratio of about 4.75; wherein said contacting proceeds under atmospheric pressure and in the presence of a strip gas; wherein said strip gas is argon; and whereby acrylic acid is produced as a result of said contacting in said reactor with a yield of at least about 30 mol %.

In yet another embodiment of the present invention, a method of making acrylic acid, acrylic acid derivatives, or mixtures thereof is provided. The method comprises contacting a feed stream comprising 2-APA with a molten salt catalyst in a reactor at 220° C.; wherein said molten salt catalyst comprises ethyltriphenylphosphonium bromide ([$EtPPh_3$]Br) and hydrobromic acid (HBr) at a molar ratio of about 4; wherein said contacting proceeds under atmospheric pressure; and whereby acrylic acid is produced as a result of said contacting in said reactor with an acrylic acid yield of at least about 25 mol %.

In even yet another embodiment of the present invention, a method of making acrylic acid, acrylic acid derivatives, or mixtures thereof is provided. The method comprises contacting a feed stream comprising lactide with a molten salt catalyst in a reactor at 150° C.; wherein said molten salt catalyst comprises [$PBu_4$]Br and 2-bromopropionic acid (2-BrPA) at a molar ratio of about 20; wherein said contacting proceeds under atmospheric pressure; and whereby acrylic acid is produced as a result of said contacting in said reactor with an acrylic acid yield of at least about 52 mol %.

DETAILED DESCRIPTION OF THE INVENTION

I Definitions

As used herein, the term "fossil-derived" material refers to a material that is produced from fossil resources, such as crude oil (petroleum), natural gas, coal, peat, etc.

As used herein, the term "non-fossil-derived" material refers to a material that is produced from non-fossil resources. For clarity and for the purposes of the present invention, the terms "renewable" material, "bio-based" material, "non-petroleum" material, and "non-fossil-derived" material are used interchangeably.

As used herein, the term "renewable" material refers to a material that is produced from a renewable resource, which is a resource produced via a natural process at a rate comparable to its rate of consumption (e.g., within a 100 year time frame). The renewable resource can be replenished naturally or via agricultural techniques. Non-limiting examples of renewable resources include plants (such as sugar cane, beets, corn, potatoes, citrus fruit, woody plants, lignocellulose, hemicellulose, and cellulosic waste), animals, fish, bacteria, fungi, and forestry products. These resources can be naturally occurring, hybrids, or genetically engineered organisms. Fossil resources take longer than 100 years to form and thus they are not considered renewable resources.

As used herein, the term "renewable content" refers to the amount of carbon from a renewable resource in a material as a percent of the weight (mass) of the total organic carbon in the material, as determined by ASTM D6866-10 Method B.

As used herein, the term "chemically inert" material refers to a material which remains in the same chemical form, under equilibrium conditions, when contacted with another material or materials. In the context of the present invention, more than about 90 wt % of the material should remain in the same chemical form to be considered a "significantly chemically inert" material and more than about 98 wt % of the material should remain in the same chemical form to be considered an "essentially chemically inert" material.

As used herein, the term "strip gas" refers to a gas that is used to physically separate one or more components from a liquid stream. Typically a strip gas is made to interact with a liquid stream in either co-current or counter-current flows to allow volatile components in the liquid stream to partition into the strip gas and be carried away by the gas stream for subsequent collection.

As used herein, the term "better leaving group" refers to a chemical group attached to the α carbon position of lactic acid that can be removed easier (e.g. milder operating conditions, or lower activation energy, or faster removal rate, etc.) than the α carbon hydroxyl group of lactic acid in a dehydration reaction. Better leaving groups are better able to stabilize the additional electron density that results from bond heterolysis than the hydroxide anion; i.e., better leaving groups exhibit lower ΔG's for elimination than the ΔG for elimination of the hydroxide anion. A list of better leaving groups than the hydroxyl group can be found in Table 10.10 of J. March, *Advanced Organic Chemistry—Reactions, Mechanisms, and Structure*, 4$^{th}$ Ed., Wiley 1992, with specific examples of better leaving groups being: $—N_2^+$, $—OR_2^+$, $—OSO_2F$, $OSO_2CF_3$, $—I$, $—Br$, $—Cl$, $—F$, $—OH_2^+$, $—NH_3^+$, and $—OAr$.

As used herein, the terms "LA" refers to lactic acid, "AA" refers to acrylic acid, "AcH" refers to acetaldehyde, and "PA" refers to propionic acid.

As used herein, the term "IL" means a salt in the liquid state.

As used herein, the term "lactic acid equivalent" refers to the lactic acid mols contained within lactic acid, lactide, or mixtures thereof. As such, the lactic acid equivalent of 1 mol of lactic acid is 1 mol, the lactic acid equivalent of 1 mol of lactide is 2 mols of lactic acid, and the lactic acid equivalent of 1 mol of a mixture of lactic acid and lactide depends on the mol fraction of lactic acid in the mixture.

As used herein, the term "conversion" in mol % is defined as [lactic acid, lactic acid derivatives, or mixtures thereof flow rate in (mol/min)–lactic acid, lactic acid derivatives, or mixtures thereof flow rate out (mol/min)]/[lactic acid, lactic acid derivatives, or mixtures thereof flow rate in (mol/min)]×100.

As used herein, the term "yield" in mol % is defined as [product flow rate out (mol/min)/lactic acid, lactic acid derivatives, or mixtures thereof flow rate in (mol/min)]×100.

As used herein, the term "selectivity" in mol % is defined as [Yield/Conversion]×100.

As used herein, the term "Weight Hourly Space Velocity" or "WHSV" in $h^{-1}$ is defined as 60×[Total lactic acid flow rate (g/min)/catalyst weight (g)]. For the purpose of this definition, the catalyst weight does not include the weight of any inert support.

As used herein, the term "standard Gibbs free energy of formation of oxide" in kJ/mol is defined as the change in Gibbs free energy that accompanies the formation of 1 mol of oxide in its standard state from its constituent elements in their standard states (1 bar pressure and 298.15° K or 25° C.), as is well known to those skilled in the art. The typical notation for the standard Gibbs free energy is $\Delta G_f^o$.

As used herein, the term "$pK_a$" is the negative base-10 logarithm of the acid dissociation constant of a solution of the acid in water at 25° C., as is well known to those skilled in the art.

As used herein, the terms "molten salt catalyst", "reactor medium", and "reaction medium" are used interchangeably.

As used herein, the term "reaction mixture" refers to the mixture of feed materials, catalysts, reactants, and products present in the reactor.

II. Catalysts for the Dehydration of Lactic Acid or its Derivatives to Acrylic Acid or its Derivatives Unexpectedly, it has been found that molten salt catalysts comprising an IL and an acid (either Lewis acid, Brønsted acid, or mixtures thereof) can dehydrate lactic acid, lactic acid derivatives, or mixtures thereof to acrylic acid, acrylic acid derivatives, or mixtures thereof with high yield and selectivity (i.e., low amount and few side products). The acid is soluble in the IL and the IL has a bromide anion ($Br^-$). Furthermore, the Lewis acid is selected from the group consisting of $CaBr_2$, $MgBr_2$, $AlBr_3$, $CuBr_2$, and mixtures thereof, and the Brønsted acid has a pKa less than about 5 in water at 25° C. Although not wishing to be bound by any theory, applicants hypothesize that the combination of the IL and acid causes the substitution of the oxygen-containing group at the α carbon of lactic acid or lactic acid derivatives by the $Br^-$ of the IL. The $Br^-$ is then either removed in a subsequent elimination reaction along with a proton from the β carbon or isomerized to the β carbon and then removed in a subsequent elimination reaction along with a proton from the α carbon (the proton removal is assisted by the conjugate base of the acid) to form the double bond in acrylic acid or acrylic acid derivatives. Also, applicants hypothesize that the Lewis acid comprises an oxophilic metal having a standard Gibbs free energy of oxide formation lower than about −600 kJmol and $Br^-$ such that the net charge of the Lewis acid is 0.

For the purposes of the present invention, the term "molten salt catalyst" refers to a catalyst that comprises an IL and an acid. ILs are salts in the liquid state, and in some context, the term refers to salts with a melting temperature below the boiling point of water. While typical liquids are made of electrically neutral molecules, ILs are primarily made of poorly-coordinated ions and short-lived ion pairs. Other names for ILs found in the literature are "room temperature molten salts", "low temperature molten salts", "ambient temperature molten salt", "ionic melts", "ionic fluids", "fused salts", "ionic glasses", "liquid electrolytes", and "liquid organic salt". Non-limiting examples of ILs are 1-ethyl-3-methylimidazolium chloride, 1-butyl-3-methylimidazolium chloride, 1-ethyl-3-methylimidazolium methanesulfonate, 1-butyl-3-methylimidazolium methanesulfonate, methylimidazolium chloride, 1-ethyl-3-methylimidazolium acetate, 1-ethyl-3-methylimidazolium ethyl sulfate, 1-ethyl-3-methylimidazolium thiocyanate, 1-butyl-3-methylimidazolium hexafluorophosphate, 1-ethyl-3-methylimidazolium tetrafluoroborate, tetrabutylphosphonium bromide, tetrabutylammonium bromide, 1-butylpyridinium bromide, 1-butyl-1-methylpyrrolidinium chloride, and tetrahexylammonium iodide.

As salts, ILs have an anion and a cation. In one embodiment of the present invention, said IL has an organic cation. In another embodiment of the present invention, said IL has an organic cation selected from the group consisting of imidazolium, pyridinium, pyrrolidinium, ammonium, phosphonium, their derivatives, and mixtures thereof. In yet another embodiment of the present invention, said IL has a phosphonium cation. In even yet another embodiment of the present invention, said phosphonium cation is selected from the group consisting of alkyl substituted phosphonium cations, aryl substituted phosphonium cations, mixed alkyl aryl substituted phosphonium cations, and mixtures thereof. Non-limiting examples of alkyl substituted phosphonium cations are tetrabutylphosphonium, tributylethylphosphonium, dibutyldiethylphosphonium, and butyltriethylphosphonium. Non-limiting examples of aryl substituted phosphonium cations are tetraphenylphosphonium, triphenyl-p-tolylphosphonium, diphenyl-di-p-tolylphosphonium, phenyl-tri-p-tolylphosphonium, and tetra-p-tolylphosphonium. Non-limiting examples of alkyl aryl substituted phosphonium cations are ethyl-triphenylphosphonium, diethydiphenylphosphonium, triethylphenylphosphonium, tributylphenylphosphonium, and tributyl-p-tolylphosphonium. In one embodiment of the present invention, said IL has a tetrabutylphosphonium cation. In another embodiment of the present invention, said IL has an ethyltriphenylphosphonium cation. In another embodiment of the present invention, said IL has an organic anion. In yet another embodiment of the present invention, said organic anion is selected from the group consisting of alkylsulfate, tosylate, methanesulfonate, and mixtures thereof. In one embodiment of the present invention, said IL has an inorganic anion. In another embodiment of the present invention, said inorganic anion is selected from the group consisting of chloride ($Cl^-$), bromide ($Br^-$), iodide ($I^-$), tetrafluoroborate ($BF_4^-$), hexafluorophosphate ($PF_6^-$), bis(trifluoromethylsulfonyl) amide, and mixtures thereof. In yet another embodiment of the present invention, said inorganic anion is bromide ($Br^-$). In even yet another embodiment of the present invention, said IL has a bromide ($Br^-$) anion and a phosphonium cation. In one embodiment of the present invention, said IL is tetrabutylphosphonium bromide ($[PBu_4]Br$). In another embodiment of the present invention, said IL is ethyltriphenylphosphonium bromide ($[EtPPh_3]Br$).

In one embodiment of the present invention, said acid is soluble in said IL and selected from the group consisting of Lewis acid, Brønsted acid, and mixtures thereof. In another embodiment of the present invention, said acid is a Brønsted acid. In yet another embodiment of the present invention, said Brønsted acid has a $pK_a$ less than about 5 in water at 25° C. Non-limiting examples of Brønsted acids with a $pK_a$ less than about 5 in water at 25° C. are acetic acid ($CH_3CO_2H$), phosphoric acid ($H_3PO_4$), pyrophosphoric acid ($H_4P_2O_7$), sulfuric acid ($H_2SO_4$), hydrobromic acid (HBr), 2-bromopropionic acid (2-BrPA), 3-bromopropionic acid (3-BrPA), hydrochloric acid (HCl), and nitric acid ($HNO_3$). In one embodiment of the present invention, said Brønsted acid is pyrophosphoric acid ($H_4P_2O_7$). In another embodiment of the present invention, said Brønsted acid is hydrobromic acid (HBr). In yet another embodiment of the present invention, said Brønsted acid is sulfuric acid ($H_2SO_4$). In even yet another embodiment of the present invention, said Brønsted acid is phosphoric acid ($H_3PO_4$). In one embodiment of the present invention, said Brønsted acid is acetic acid ($CH_3CO_2H$). In another embodiment of the present invention, said Brønsted acid is 2-bromopropionic acid (2-BrPA). In yet another embodiment of the present invention, said Brønsted acid is 3-bromopropionic acid (3-BrPA). In one embodiment of the present invention, said 2-bromoprionic acid is prepared by the reaction of lactic acid or lactide and 3-methyl-1-(4-butane sulfonic acid) imidazolium bromide ([MIMBS]Br). In another embodiment of the present invention, said 2-bromoprionic acid is prepared by the reaction of lactic acid or lactide and 3-methyl-1-(4-butane sulfonic acid) imidazolium bromide ([MIMBS]Br) at a temperature from about 100° C. to about 140° C., at a molar ratio of [MIMBS]Br to lactic acid from about 1:1 to about 6:1, and reaction time of about 5 hours.

In one embodiment of the present invention, said acid is a Lewis acid. In another embodiment of the present invention, said acid is a mixture of a Lewis acid and a Brønsted acid. In yet another embodiment of the present invention, said Lewis acid is selected from the group consisting of $CaBr_2$, $MgBr_2$, $AlBr_3$, $CuBr_2$, and mixtures thereof. In even yet another embodiment of the present invention, said Lewis acid comprises an oxophilic metal having a standard Gibbs free energy of oxide formation lower than about −600 kJmol and $Br^-$ such that the net charge of the Lewis acid is 0. Non-limiting examples of Lewis acids comprising an oxophilic metal having a standard Gibbs free energy of oxide formation lower than about −600 kJmol and $Br^-$ such that the net charge of the Lewis acid is 0 are $CaBr_2$, $MgBr_2$, $AlBr_3$, $BaBr_2$, $SiBr_4$, $BeBr_2$, $CrBr_6$, and $WBr_6$.

In one embodiment of the present invention, the oxophilic metal has an oxidation state ranging from +1 to +6. In another embodiment of the present invention, the oxophilic metal has an oxidation state of +2 or +3. In yet another embodiment of the present invention, the oxophilic metal has an oxidation state of +4 or +5 or +6.

In one embodiment of the present invention, the molar ratio of said Brønsted acid to said Lewis acid is between about 0.1 and about 10. In yet another embodiment of the present invention, the molar ratio of said Brønsted acid to said Lewis acid is between about 0.5 and about 5. In even yet another embodiment of the present invention, the molar ratio of said Brønsted acid to said Lewis acid is about 1.

In one embodiment of the present invention, said IL is tetrabutylphosphonium bromide ($[PBu_4]Br$) and said acid is pyrophosphoric acid ($H_4P_2O_7$). In another embodiment of the present invention, said IL is tetrabutylphosphonium bromide ($[PBu_4]Br$) and said acid is acetic acid ($CH_3CO_2H$). In yet another embodiment of the present invention, said IL is $[PBu_4]Br$ and said acid is selected from the group consisting of $CaBr_2$, $MgBr_2$, $AlBr_3$, $CuBr_2$, and mixtures thereof. In even yet another embodiment of the present invention, said IL is tetrabutylphosphonium bromide ([PBu$_4$]Br) and said acid is sulfuric acid (H$_2$SO$_4$). In one embodiment of the present invention, said IL is tetrabutylphosphonium bromide ([PBu$_4$]Br) and said acid is hydrobromic acid (HBr). In another embodiment of the present invention, said IL is ethyltriphenlphosphonium bromide ([EtPPh$_3$]Br) and said acid is hydrobromic acid (HBr). In yet another embodiment of the present invention, said IL is tetrabutylphosphonium bromide ([PBu$_4$]Br) and said acid consists of HBr and a Lewis acid selected from the group consisting of CaBr$_2$, MgBr$_2$, AlBr$_3$, CuBr$_2$, and mixtures thereof. In even yet another embodiment of the present invention, said IL is tetrabutylphosphonium bromide ([PBu$_4$]Br) and said acid is 2-bromopropionic acid (2-BrPA). In one embodiment of the present invention, said IL is tetrabutylphosphonium bromide ([PBu$_4$]Br) and said acid is 3-bromopropionic acid (3-BrPA).

In one embodiment of the present invention, the molar ratio of said IL to said acid is between about 1 and about 30. In another embodiment of the present invention, the molar ratio of said IL to said acid is between about 2 and about 15. In yet another embodiment of the present invention, the molar ratio of said IL to said acid is between about 3 and about 7. In even yet another embodiment of the present invention, the molar ratio of said IL to said acid is about 4. In one embodiment of the present invention, the molar ratio of said IL to said acid is about 4.75. In another embodiment of the present invention, the molar ratio of said IL to said acid is about 10. In yet another embodiment of the present invention, the molar ratio of said IL to said acid is about 20.

In one embodiment of the present invention, the molar ratio of said [PBu$_4$]Br and said H$_4$P$_2$O$_7$ is between about 1 and about 30. In another embodiment of the present invention, the molar ratio of said [PBu$_4$]Br and said H$_4$P$_2$O$_7$ is between about 3 and about 10. In yet another embodiment of the present invention, the molar ratio of said [PBu$_4$]Br and said H$_4$P$_2$O$_7$ is between about 3.5 and about 7. In even yet another embodiment of the present invention, the molar ratio of said [PBu$_4$]Br and said H$_4$P$_2$O$_7$ is about 4.75.

In one embodiment of the present invention, the molar ratio of said [PBu$_4$]Br and said HBr is between about 1 and about 20. In another embodiment of the present invention, the molar ratio of said [PBu$_4$]Br and said HBr is between about 2 and about 10. In yet another embodiment of the present invention, the molar ratio of said [PBu$_4$]Br and said HBr is between about 2 and about 5. In even yet another embodiment of the present invention, the molar ratio of said [PBu$_4$]Br and said HBr is about 4.75.

In one embodiment of the present invention, the molar ratio of said [EtPPh$_3$]Br and said HBr is between about 1 and about 20. In another embodiment of the present invention, the molar ratio of said [EtPPh$_3$]Br and said HBr is between about 2 and about 10. In yet another embodiment of the present invention, the molar ratio of said [EtPPh$_3$]Br and said HBr is between about 2 and about 5. In even yet another embodiment of the present invention, the molar ratio of said [EtPPh$_3$]Br and said HBr is about 4.

In one embodiment of the present invention, the molar ratio of said [PBu$_4$]Br and said H$_2$SO$_4$ is between about 3 and about 10. In another embodiment of the present invention, the molar ratio of said [PBu$_4$]Br and said H$_2$SO$_4$ is between about 3.5 and about 7. In yet another embodiment of the present invention, the molar ratio of said [PBu$_4$]Br and said H$_2$SO$_4$ is between about 4 and about 5. In even yet another embodiment of the present invention, the molar ratio of said [PBu$_4$]Br and said H$_2$SO$_4$ is about 4.75.

In one embodiment of the present invention, the molar ratio of said [PBu$_4$]Br and said H$_3$PO$_4$ is between about 3 and about 10. In another embodiment of the present invention, the molar ratio of said [PBu$_4$]Br and said H$_3$PO$_4$ is between about 3.5 and about 7. In yet another embodiment of the present invention, the molar ratio of said [PBu$_4$]Br and said H$_3$PO$_4$ is between about 4 and about 5. In even yet another embodiment of the present invention, the molar ratio of said [PBu$_4$]Br and said H$_3$PO$_4$ is about 4.75.

In one embodiment of the present invention, the molar ratio of said [PBu$_4$]Br and said acetic acid (CH$_3$CO$_2$H) is between about 3 and about 10. In another embodiment of the present invention, the molar ratio of said [PBu$_4$]Br and said acetic acid (CH$_3$CO$_2$H) is between about 3.5 and about 7. In yet another embodiment of the present invention, the molar ratio of said [PBu$_4$]Br and said acetic acid (CH$_3$CO$_2$H) is between about 4 and about 5. In even yet another embodiment of the present invention, the molar ratio of said [PBu$_4$]Br and said acetic acid (CH$_3$CO$_2$H) is about 4.75.

In one embodiment of the present invention, the molar ratio of said [PBu$_4$]Br and said 2-bromopropionic acid (2-BrPA) is about 10. In another embodiment of the present invention, the molar ratio of said [PBu$_4$]Br and said 2-bromopropionic acid (2-BrPA) is about 20. In yet another embodiment of the present invention, the molar ratio of said [PBu$_4$]Br and said 3-bromopropionic acid (3-BrPA) is about 10. In even yet another embodiment of the present invention, the molar ratio of said [PBu$_4$]Br and said 3-bromopropionic acid (3-BrPA) is about 20.

In one embodiment of the present invention, the molar ratio of said [PBu$_4$]Br and said CaBr$_2$ is about 4.75. In another embodiment of the present invention, the molar ratio of said [PBu$_4$]Br and said MgBr$_2$ is about 4.75. In yet another embodiment of the present invention, the molar ratio of said [PBu$_4$]Br and said AlBr$_3$ is about 4.75. In even yet another embodiment of the present invention, the molar ratio of said [PBu$_4$]Br and said CuBr$_2$ is about 4.75. In one embodiment of the present invention, the molar ratio of said [PBu$_4$]Br and said equimolar mixture of HBr and AlBr$_3$ is about 4.75. In another embodiment of the present invention, the molar ratio of HBr and AlBr$_3$ is between about 0.1 and about 10. In yet another embodiment of the present invention, the molar ratio of HBr and AlBr$_3$ is between about 0.5 and about 5. In even yet another embodiment of the present invention, the molar ratio of HBr and AlBr$_3$ is about 1.

In one embodiment of the present invention, the molten salt catalyst comprising an IL and an acid further comprises other compound which is significantly chemically inert to said IL and acid. In another embodiment of the present invention, said other compound comprises a cation and an anion. Non-limiting examples of anions in the other compound are arsenates, condensed arsenates, nitrates, sulfates, condensed sulfates, borates, carbonates, chromates, condensed chromates, vanadates, niobates, tantalates, selenates, condensed silicates, condensed aluminates, germanates, condensed germanates, molybdates, condensed molybdates, other monomeric oxyanions, polyoxyanions, heteropolyphosphates, such as arsenatophosphates, phosphoaluminates, phosphoborates, phosphochromates, phosphomolybdates, phosphosilicates, phosphosulfates, phosphotungstates, and phosphate adducts, such as phosphate anions with telluric acid, halides, borates, carbonates, nitrates, sulfates, chromates, silicates, oxalates, mixtures thereof, or others that may be apparent to those having ordinary skill in the art.

In one embodiment of the present invention, said molten salt catalyst further comprises an inert support. Non-limiting examples of inert supports are silica, silicate, alumina, aluminate, aluminosilicate, titania, titanate, zirconia, zirconate, carbon (such as activated carbon, diamond, graphite, or fullerenes), sulfate, phosphate, tantalate, ceria, other metal oxides, and mixtures thereof. In another embodiment of the present invention, said inert support consists essentially of silica. In yet another embodiment of the present invention, said silica is selected from the group consisting of amorphous silica, quartz, tridymite, cristobalite, moganite, coesite, and mixtures thereof. In even yet another embodiment of the present invention, said silica is amorphous silica. In one embodiment of the present invention, said silica has a specific surface area of less than about 10 $m^2/g$. In another embodiment of the present invention, the inert support represents an amount between about 20 wt % and about 90 wt %, based on the total weight of the active catalyst.

In one embodiment of the present invention, the weight of the IL and acid based on the total weight of the molten salt catalyst is about 100 wt %. In another embodiment of the present invention, the weight of the IL and acid based on the total weight of the molten salt catalyst is between about 5 wt % and about 90 wt %. In yet another embodiment of the present invention, the weight of the IL and acid based on the total weight of the molten salt catalyst is between about 20 wt % and about 80 wt %. In even yet another embodiment of the present invention, the weight of the IL and acid based on the total weight of the molten salt catalyst is between about 40 wt % and about 60 wt %. In one embodiment of the present invention, the weight of the IL and acid based on the total weight of the molten salt catalyst is about 50 wt %.

In one embodiment of the present invention, the catalyst for making acrylic acid, acrylic acid derivatives, or mixtures thereof is a molten salt and comprises an IL and an acid. In another embodiment of the present invention, the catalyst for making acrylic acid, acrylic acid derivatives, or mixtures thereof is a molten salt and comprises an IL and an acid; wherein the IL is tetrabutylphosphonium bromide ([PBu$_4$]Br) and the acid is pyrophosphoric acid ($H_4P_2O_7$); wherein the molar ratio of [PBu$_4$]Br and $H_4P_2O_7$ is about 4.75; and whereby the acrylic acid is produced with a yield of at least about 30 mol %. In yet another embodiment of the present invention, the catalyst for making acrylic acid, acrylic acid derivatives, or mixtures thereof is a molten salt and comprises an IL and an acid; wherein the IL is tetrabutylphosphonium bromide ([PBu$_4$]Br) and the acid is hydrobromic acid (HBr); wherein the molar ratio of [PBu$_4$]Br and HBr is between about 2 and about 5; and whereby the acrylic acid is produced with a yield of at least about 18 mol %. In yet another embodiment of the present invention, a catalyst for making acrylic acid, acrylic acid derivatives, or mixtures thereof by dehydrating lactic acid, lactic acid derivatives, or mixtures thereof; wherein said catalyst is a molten salt and comprises an IL and an acid; wherein said IL is ethyltriphenylphosphonium bromide ([EtPPh$_3$]Br) and said acid is hydrobromic acid (HBr); wherein the molar ratio of said [EtPPh$_3$]Br to said HBr is between about 2 and about 5; and whereby said acrylic acid is produced with a yield of at least about 25 mol %. In even yet another embodiment of the present invention, the catalyst for making acrylic acid, acrylic acid derivatives, or mixtures thereof is a molten salt and comprises an IL and an acid; wherein the IL is tetrabutylphosphonium bromide ([PBu$_4$]Br) and the acid is 2-bromopropionic acid (2-BrPA); wherein the molar ratio of [PBu$_4$]Br and 2-BrPA is about 10; and whereby the acrylic acid is produced with a yield of at least about 47 mol %. In even yet another embodiment of the present invention, the catalyst for making acrylic acid, acrylic acid derivatives, or mixtures thereof is a molten salt and comprises an IL and an acid; wherein the IL is tetrabutylphosphonium bromide ([PBu$_4$]Br) and the acid is 3-bromopropionic acid (3-BrPA); wherein the molar ratio of [PBu$_4$]Br and 3-BrPA is about 10; and whereby the acrylic acid is produced with a yield of at least about 47 mol %. In one embodiment of the present invention, the catalyst for making acrylic acid, acrylic acid derivatives, or mixtures thereof is a molten salt and comprises an IL and an acid; wherein the IL is tetrabutylphosphonium bromide ([PBu$_4$]Br) and the acid is 2-bromopropionic acid (2-BrPA); wherein the molar ratio of [PBu$_4$]Br and 2-BrPA is about 20; and whereby the acrylic acid is produced with a yield of at least about 52 mol %. In even yet another embodiment of the present invention, the catalyst for making acrylic acid, acrylic acid derivatives, or mixtures thereof is a molten salt and comprises an IL and an acid; wherein the IL is tetrabutylphosphonium bromide ([PBu$_4$]Br) and the acid is 3-bromopropionic acid (3-BrPA); wherein the molar ratio of [PBu$_4$]Br and 3-BrPA is about 20; and whereby the acrylic acid is produced with a yield of at least about 52 mol %.

Besides an IL and an acid, the molten salt catalyst of the present invention can include a phospine oxide OPX$_3$, where X can be selected from a variety of groups. Non-limiting examples of phosphine oxides are triphenylphosphine oxide (TPPO), tributylphosphine oxide (TBPO), triethylphosphine oxide (TEPO), and trioctylphosphine oxide (TOPO).

The molten salt catalyst of the present invention can be utilized to catalyze several chemical reactions. Non-limiting examples of reactions are: dehydration of lactic acid, lactic acid derivatives, or mixtures thereof to acrylic acid; dehydration of 3-hydroxypropionic acid, 3-hydroxypropionic acid derivatives, or mixtures thereof to acrylic acid; dehydration of glycerin to acrolein; isomerization of lactic acid to 3-hydroxypropionic acid in the presence of water; reduction of hydroxypropionic acid to propionic acid or 1-propanol in the presence of hydrogen gas; dehydration of aliphatic alcohols to alkenes or olefins; dehydrogenation of aliphatic alcohols to ethers; other dehydrogenations, hydrolyses, alkylations, dealkylations, oxidations, disproportionations, esterifications, cyclizations, isomerizations, condensations, aromatizations, polymerizations; and other reactions that may be apparent to those having ordinary skill in the art.

III Methods of Making Acrylic Acid, Acrylic Acid Derivatives, or Mixtures Thereof A method of dehydrating hydroxypropionic acid, hydroxypropionic acid derivatives, or mixtures thereof to acrylic acid, acrylic acid derivatives, or mixtures thereof is provided. In one embodiment of the present invention, said hydroxypropionic acid is selected from the group consisting of lactic acid (2-hydroxypropionic acid), 3-hydroxypropionic acid, and mixtures thereof; and said hydroxypropionic acid derivatives are selected from the group consisting of lactic acid derivatives, 3-hydroxypropionic acid derivatives, and mixtures thereof.

In another embodiment of the present invention, said hydroxypropionic acid is lactic acid and said hydroxypropionic acid derivatives are lactic acid derivatives. Lactic acid can be D-lactic acid, L-lactic acid, or mixtures thereof (including racemic mixture). It is well known to those skilled in the art that the at carbon hydroxyl group of lactic acid is not a good leaving group and that the carboxylic group of lactic acid is prone to decarboxylation or decarbonylation. This decarboxylation and decarbonylation is easier than the removal of the hydroxyl group, and that is the reason that many past attempts failed to produce commercially-viable quantities of acrylic acid. Although not wishing to be bound by any theory, applicants believe that commercially-viable quantities of acrylic acid can be produced from lactic acid if the hydroxyl group is replaced by a better leaving group, the carboxylic group is protected, or both the hydroxyl group is replaced by a better leaving group and the carboxylic group is protected.

Non-limiting examples of lactic acid derivatives with their carboxylic group protected are metal or ammonium salts of lactic acid (also called metal or ammonium lactates), alkyl esters of lactic acid (also called alkyl lactates), cyclic di-esters of lactic acid, or mixtures thereof. Non-limiting examples of metal lactates are sodium lactate, potassium lactate, and calcium lactate; non-limiting examples of alkyl lactates are methyl lactate (MLA), ethyl lactate (ELA), butyl lactate, and 2-ethylhexyl lactate; and a non-limiting example of cyclic di-esters of lactic acid is dilactide (also called lactide).

Non-limiting examples of lactic acid derivatives with their hydroxyl group replaced by a better leaving group are 2-alkoxypropionic acids, 2-aryloxypropionic acids, 2-acyloxypropionic acids, 2-fluoropropionic acid (2-FPA), 2-chloropropionic acid (2-ClPA), 2-bromopropionic acid (2-BrPA), 2-iodopropionic acid (2-IPA), or mixtures thereof. Non-limiting examples of 2-alkoxypropionic acids are 2-methoxypropionic acid and 2-ethoxypropionic acid; a non-limiting example of 2-aryloxypropionic acid is 2-phenoxypropionic acid; and non-limiting examples of 2-acyloxypropionic acid is 2-acetoxypropionic acid (2-APA) and 2-trifluoroacetoxypropionic acid (2-TFPA).

Non-limiting examples of lactic acid derivatives with both their hydroxyl group replaced by a better leaving group and their carboxylic group protected are alkyl esters of 2-alkoxypropionic acid, alkyl esters of 2-aryloxypropionic acid, alkyl esters of 2-acyloxypropionic acid, or mixtures thereof. Non-limiting examples of alkyl esters of 2-alkoxypropionic acid are ethyl 2-methoxypropionate and methyl 2-ethoxypropionate; non-limiting examples of alkyl esters of 2-aryloxypropionic acid are methyl 2-phenoxypropionate and ethyl 2-phenoxypropionate; and non-limiting examples of alkyl esters of 2-acyloxypropionic acid are methyl 2-acetoxypropionate (MAPA), ethyl 2-acetoxypropionate (EAPA), and ethyl 2-trifluoacetoxypropionate (ETFP).

In one embodiment of the present invention, the lactic acid derivatives are selected from the group consisting of lactic acid with its carboxylic group protected, lactic acid with its hydroxyl group replaced by a better leaving group, lactic acid with both its carboxylic group protected and hydroxyl group replaced by a better leaving group, and mixtures thereof. In another embodiment of the present invention, the lactic acid derivatives are selected from the group consisting of lactide, 2-acetoxypropionic acid (2-APA), ETFP, and 2-bromopropionic acid (2-BrPA). In yet another embodiment of the present invention, the lactic acid derivative is ETFP. Other lactic acid derivatives can be lactic acid oligomers, lactic acid anhydride, and 3-bromopropionic acid (3-BrPA).

Lactic acid can be in monomeric form or as oligomers in said feed stream. In one embodiment of the present invention, the oligomers of the lactic acid in said feed stream are less than about 30 wt % based on the total amount of lactic acid, lactic acid derivatives, or mixtures thereof. In another embodiment of the present invention, the oligomers of the lactic acid in said feed stream are less than about 10 wt % based on the total amount of lactic acid, lactic acid derivatives, or mixtures thereof. In yet another embodiment of the present invention, the oligomers of the lactic acid feed stream are less than about 5 wt % based on the total amount of lactic acid, lactic acid derivatives, or mixtures thereof. In even yet another embodiment of the present invention, the lactic acid is essentially in monomeric form in said feed stream.

The process to remove the oligomers from the feed stream can comprise a purification step or hydrolysis by heating step. In one embodiment of the present invention, the heating step can involve heating the feed stream at a temperature between about 50° C. and about 100° C. to hydrolyze the oligomers of the lactic acid. In another embodiment of the present invention, the heating step can involve heating the feed stream at a temperature between about 95° C. and about 100° C. to hydrolyze the oligomers of the lactic acid. In yet another embodiment of the present invention, the heating step can involve heating the feed stream at a temperature between about 50° C. and about 100° C. to hydrolyze the oligomers of the lactic acid and produce a monomeric lactic acid feed stream comprising at least 80 wt % of lactic acid in monomeric form based on the total amount of lactic acid, lactic acid derivatives, or mixtures thereof. In even yet another embodiment of the present invention, the heating step can involve heating the feed stream at a temperature between about 50° C. and about 100° C. to hydrolyze the oligomers of the lactic acid and produce a monomeric lactic acid feed stream comprising at least 95 wt % of lactic acid in monomeric form based on the total amount of lactic acid, lactic acid derivatives, or mixtures thereof. In one embodiment of the present invention, an about 88 wt % aqueous solution of lactic acid, lactic acid derivatives, or mixtures thereof is diluted with water and the oligomers are hydrolyzed to produce an aqueous solution of about 20 wt % lactic acid.

3-hydroxypropionic acid derivatives can be metal or ammonium salts of 3-hydroxypropionic acid, alkyl esters of 3-hydroxypropionic acid, 3-hydroxypropionic acid oligomers, 3-alkoxypropionic acids or their alkyl esters, 3-aryloxypropionic acids or their alkyl esters, 3-acyloxypropionic acids or their alkyl esters, or a mixture thereof. Non-limiting examples of metal salts of 3-hydroxypropionic acid are sodium 3-hydroxypropionate, potassium 3-hydroxypropionate, and calcium 3-hydroxypropionate. Non-limiting examples of alkyl esters of hydroxypropionic acid are methyl 3-hydroxypropionate, ethyl 3-hydroxypropionate, butyl 3-hydroxypropionate, 2-ethylhexyl 3-hydroxypropionate, and mixtures thereof. Non-limiting examples of 3-alkoxypropionic acids are 3-methoxypropionic acid and 3-ethoxypropionic acid. A non-limiting example of 3-aryloxypropionic acid is 3-phenoxypropionic acid. A non-limiting example of 3-acyloxypropionic acid is 3-acetoxypropionic acid.

Hydroxypropionic acid, hydroxypropionic acid derivatives, or mixtures thereof can be produced by sugar fermentation or chemical conversion of sugars or other feedstock materials, such as glycerin. Nearly all world production of lactic acid is by sugar fermentation today; however, there are chemical conversion technologies currently in pilot or demo scale. Also, the sugar feedstock can be generation 1 sugar (i.e., sugar from corn, sugarcane, sugar beets, wheat, potato, rice, etc.) or generation 2 sugar (i.e., sugar from the hydrolysis of biomass or agricultural waste, such as bagasse, corn stover, rice husk, wheat straw, etc.).

Acrylic acid derivatives can be metal or ammonium salts of acrylic acid, alkyl esters of acrylic acid, acrylic acid oligomers, or mixtures thereof. Non-limiting examples of metal salts of acrylic acid are sodium acrylate, potassium acrylate, and calcium acrylate. Non-limiting examples of alkyl esters of acrylic acid are methyl acrylate, ethyl acrylate, butyl acrylate, 2-ethylhexyl acrylate, or mixtures thereof.

In one embodiment of the present invention, the feed stream comprises a liquid. In another embodiment of the present invention, the feed stream comprises a solid. In yet another embodiment of the present invention, the feed stream comprises a liquid and a solid. In even yet another embodiment of the present invention, the feed stream comprises a liquid and a gas.

In one embodiment of the present invention, a method of making acrylic acid, acrylic acid derivatives, or mixtures thereof comprises contacting a feed stream comprising lactic acid, lactic acid derivatives, or mixtures thereof with a molten salt catalyst in a reactor at a temperature, wherein the molten salt catalyst comprises an IL and an acid, and whereby acrylic acid, acrylic acid derivatives, or mixtures thereof are produced as a result of the dehydration in the reactor.

In another embodiment of the present invention, said feed stream further comprises an essentially chemically inert diluent. In the context of the present invention, an essentially chemically inert diluent is any diluent that is essentially chemically inert to said hydroxypropionic acid, hydroxypropionic acid derivatives, or mixtures thereof, but not necessarily to said molten salt catalyst. Non-limiting examples of essentially chemically inert diluents are water, hydrocarbons, chlorinated hydrocarbons, brominated hydrocarbons, fluorinated hydrocarbons, esters, ethers, ketones, and mixtures thereof. Non-limiting examples of hydrocarbons are C5 to C8 linear and branched alkanes. A non-limiting example of esters is ethyl acetate. A non-limiting example of ethers is diphenyl ether. A non-limiting example of ketones is acetone. In yet another embodiment of the present invention, said essentially chemically inert diluent comprises water. In even yet another embodiment of the present invention, said essentially chemically inert diluent consists essentially of water. In one embodiment of the present invention said feed stream consists essentially of hydroxypropionic acid, hydroxypropionic acid derivatives, or mixtures thereof.

In another embodiment of the present invention, the feed stream comprising hydroxypropionic acid, hydroxypropionic acid derivatives, or mixtures thereof can further comprise one or more antioxidants. In another embodiment of the present invention, the feed stream comprising hydroxypropionic acid, hydroxypropionic acid derivatives, or mixtures thereof further comprises butylated hydroxy toluene (BHT), butylated hydroxy anisole (BHA), or mixtures thereof. In yet another embodiment of the present invention, the feed stream comprising hydroxypropionic acid, hydroxypropionic acid derivatives, or mixtures thereof further comprises ethylene glycol, ethanedithiol, methanol, methanethiol, or mixtures thereof.

In one embodiment of the present invention, the concentration of the hydroxypropionic acid, hydroxypropionic acid derivatives, or mixtures thereof in said feed stream is between about 1 wt % and about 100 wt %. In another embodiment of the present invention, the concentration of the hydroxypropionic acid, hydroxypropionic acid derivatives, or mixtures thereof in said feed stream is between about 5 wt % and about 95 wt %. In yet another embodiment of the present invention, the concentration of the hydroxypropionic acid, hydroxypropionic acid derivatives, or mixtures thereof in said feed stream is between about 20 wt % and about 80 wt %. In even yet another embodiment of the present invention, the concentration of the hydroxypropionic acid, hydroxypropionic acid derivatives, or mixtures thereof in said feed stream is about 25 wt %. In one embodiment of the present invention, the concentration of the hydroxypropionic acid, hydroxypropionic acid derivatives, or mixtures thereof in said feed stream is about 50 wt %.

In one embodiment of the present invention, the concentration of the lactic acid, lactic acid derivatives, or mixtures thereof in said feed stream is between about 1 wt % and about 100 wt %. In another embodiment of the present invention, the concentration of the lactic acid, lactic acid derivatives, or mixtures thereof in said feed stream is between about 5 wt % and about 95 wt %. In yet another embodiment of the present invention, the concentration of the lactic acid, lactic acid derivatives, or mixtures thereof in said feed stream is between about 20 wt % and about 80 wt %. In even yet another embodiment of the present invention, the concentration of the lactic acid, lactic acid derivatives, or mixtures thereof in said feed stream is about 25 wt %. In one embodiment of the present invention, the concentration of the lactic acid, lactic acid derivatives, or mixtures thereof in said feed stream is about 50 wt %.

Non-limiting examples of reactors suitable for use in the present invention are static reactors, stirred tank reactors, recirculation reactors, trickle bed reactors, and combinations thereof. In one embodiment of the present invention, the reactor is a stirred tank reactor. In another embodiment of the present invention, the stirred tank reactor is a single-layer reactor. A single-layer reactor consists of a single layer (also called wall) that extends from the inner surface to the outer surface and has a wall thickness. The inner surface is in contact with the molten salt catalyst, the feed stream, and the product stream. In one embodiment of the present invention, the single-layer reactor comprises a wall, an outer surface, and an inner surface; wherein said wall is made from a wall material, has a wall thickness, and extends from said outer surface to said inner surface; and wherein said inner surface is in contact with said molten salt catalyst, feed stream, and product stream.

In one embodiment of the present invention, the wall thickness of a single-layer reactor is between about 2 mm and about 30 mm. In another embodiment of the present invention, the wall thickness of a single-layer reactor is between about 3 mm and about 20 mm. In yet another embodiment of the present invention, the wall thickness of a single-layer reactor is between about 4 mm and about 10 mm. In even yet another embodiment of the present invention, the wall thickness of a single-layer reactor is between about 5 mm and about 8 mm.

In one embodiment of the present invention, the stirred tank reactor is a bi-layer reactor. The bi-layer reactor comprises an inner surface, which is in contact with the molten salt catalyst, feed stream, and product stream, and is the innermost surface of the bi-layer reactor. The bi-layer reactor consists of an inner layer, which has an inner layer thickness, an outer layer, which has an outer layer thickness, an interface between the outer layer and the inner layer, and an outer surface, which is the outmost surface of the bi-layer reactor. In another embodiment of the present invention, the outer layer of the bi-layer reactor consists of two or more sublayers. In yet another embodiment of the present invention, the bi-layer reactor comprises an outer layer, an inner layer, an outer surface, an inner surface, and an interface between said outer layer and said inner layer; wherein said outer layer is made from an outer layer material, has an outer layer thickness, and extends from said interface to said outer surface; wherein said inner layer is made from an inner layer material, has an inner layer thickness, and extends from said inner surface to said interface; and wherein said inner surface is in contact with said molten salt catalyst, feed stream, and product stream. In even yet another embodiment of the present invention, said outer layer comprises two or more sublayers.

In one embodiment of the present invention, the inner layer thickness of a bi-layer reactor is between about 1 mm and about 20 mm. In another embodiment of the present invention, the inner layer thickness of a bi-layer reactor is between about 1.5 mm and about 10 mm. In yet another embodiment of the present invention, the inner layer thickness of a bi-layer reactor is between about 2 mm and about 8 mm. In even yet another embodiment of the present invention, the inner layer thickness of a bi-layer reactor is between about 3 mm and about 6 mm. In one embodiment of the present invention, the outer layer thickness of a bi-layer reactor is between about 1 mm and about 20 mm. In another embodiment of the present invention, the outer layer thickness of a bi-layer reactor is between about 1.5 mm and about 10 mm. In yet another embodiment of the present invention, the outer layer thickness of a bi-layer reactor is between about 2 mm and about 8 mm. In even yet another embodiment of the present invention, the outer layer thickness of a bi-layer reactor is between about 3 mm and about 6 mm.

The molten salt catalysts, or the feed stream, or the product stream of the present invention can be corrosive to the reactors. Non-limiting examples of materials that can be used in the present invention as either wall materials or inner layer materials are glass; silica; sapphire; titanium; copper; silver; gold; tungsten; tantalum; zirconium; HASTELLOY® and HAYNES® alloys (Ni-based alloys; Haynes International, Inc.; Kokomo, Ind.); INCONEL®, INCOLOY®, and MONEL® alloys (Ni-based alloys; Special Metals Corporation; Huntington, W. Va.); and plastic materials (e.g., polytetrafluoroethylene (PTFE), polyetherether ketone (PEEK), and polyether sulfone (PES)). In one embodiment of the present invention, the outer layer material is selected from the group consisting of stainless steel and carbon steel. In another embodiment of the present invention, the outer layer material is stainless steel and the inner layer material of the bi-layer reactor is titanium.

In one embodiment of the present invention, the single-layer reactor has a corrosion rate lower than about 1.3 mm/y. In another embodiment of the present invention, the bi-layer reactor has a corrosion rate lower than about 1.3 mm/y. For the purposes of the present invention, the corrosion rate is measured by weighing a wall material sample or an inner layer material sample before and after exposure to the reaction conditions, as this is known to those skilled in the art.

In one embodiment of the present invention, said corrosion rate is lower than about 1 mm/y. In another embodiment of the present invention, said corrosion rate is lower than about 0.5 mm/y. In yet another embodiment of the present invention, said corrosion rate is lower than about 0.13 mm/y. In even yet another embodiment of the present invention, said corrosion rate is lower than about 0.05 mm/y.

In one embodiment of the present invention, the temperature during said dehydration is greater than about 50° C. In another embodiment of the present invention, the temperature during said dehydration is between about 80° C. and about 400° C. In yet another embodiment of the present invention, the temperature during said dehydration is between about 140° C. and about 300° C. In even yet another embodiment of the present invention, the temperature during said dehydration is between about 150° C. and about 280° C. In one embodiment of the present invention, the temperature during said dehydration is between about 180° C. and about 250° C. In another embodiment of the present invention, the temperature during said dehydration is about 220° C. In yet another embodiment of the present invention, the temperature during said dehydration is about 150° C. In even yet another embodiment of the present invention, the temperature during said dehydration is about 160° C. In one embodiment of the present invention, the temperature during said dehydration is about 180° C.

The contacting of the feed stream and the molten salt catalyst can be performed under vacuum, at atmospheric pressure, or at pressure higher than atmospheric. In one embodiment of the present invention, the contacting is performed under a total pressure of at least about 1 bar. In another embodiment of the present invention, the contacting is performed under a total pressure between about 250 mbar and about 2 bar. In yet another embodiment of the present invention, the contacting is performed at atmospheric pressure.

In one embodiment of the present invention, said WHSV is between about 0.02 $h^{-1}$ and about 10 $h^{-1}$. In another embodiment of the present invention, said WHSV is between about 0.2 $h^{-1}$ and about 2 $h^{-1}$. In yet another embodiment of the present invention, said WHSV is between about 0.3 $h^{-1}$ and about 1.4 $h^{-1}$. In even yet another embodiment of the present invention, said WHSV is between about 0.3 $h^{-1}$ and about 0.4 $h^{-1}$. In one embodiment of the present invention, said WHSV is about 0.4 $h^{-1}$.

In one embodiment of the present invention, said acrylic acid, acrylic acid derivatives, or mixtures thereof are produced with a yield of at least 10 mol %. In another embodiment of the present invention, said acrylic acid, acrylic acid derivatives, or mixtures thereof are produced with a yield of at least about 20%. In yet another embodiment of the present invention, said acrylic acid, acrylic acid derivatives, or mixtures thereof are produced with a yield of at least about 30 mol %. In even yet another embodiment of the present invention, said acrylic acid, acrylic acid derivatives, or mixtures thereof are produced with a yield of at least 40 mol %. In one embodiment of the present invention, said acrylic acid, acrylic acid derivatives, or mixtures thereof are produced with a yield of at least about 60%. In another embodiment of the present invention, said acrylic acid, acrylic acid derivatives, or mixtures thereof are produced with a yield of at least about 80 mol %.

In one embodiment of the present invention, said acrylic acid, acrylic acid derivatives, or mixtures thereof are produced with a selectivity of at least about 50 mol %. In another embodiment of the present invention, said acrylic acid, acrylic acid derivatives, or mixtures thereof are produced with a selectivity of at least about 70 mol %. In yet another embodiment of the present invention, said acrylic acid, acrylic acid derivatives, or mixtures thereof are produced with a selectivity of at least about 80 mol %.

In one embodiment of the present invention, said acrylic acid, acrylic acid derivatives, or mixtures thereof are produced with a yield of at least about 10 mol % and with a selectivity of at least about 50 mol %. In another embodiment of the present invention, said acrylic acid, acrylic acid derivatives, or mixtures thereof are produced with a yield of at least about 30 mol % and with a selectivity of at least about 70 mol %. In yet another embodiment of the present invention, said acrylic acid, acrylic acid derivatives, or mixtures thereof are produced with a yield of at least about 50 mol % and with a selectivity of at least about 80 mol %.

In even yet another embodiment of the present invention, said acrylic acid, acrylic acid derivatives, or mixtures thereof are produced with a yield of at least about 80 mol % and with a selectivity of at least about 80 mol %.

In one embodiment of the present invention, propionic acid is produced as an impurity along with said acrylic acid, acrylic acid derivatives, or mixtures thereof; and wherein the selectivity of said propionic acid is less than about 5 mol %. In another embodiment of the present invention, propionic acid is produced as an impurity along with said acrylic acid, acrylic acid derivatives, or mixtures thereof; and wherein the selectivity of said propionic acid is less than about 1 mol %.

In one embodiment of the present invention, said acrylic acid, acrylic acid derivatives, or mixtures thereof are produced with a yield of at least about 10 mol % and with a selectivity of at least about 50 mol % over a TOS of about 72 h; wherein propionic acid is produced as an impurity along with said acrylic acid, acrylic acid derivatives, or mixtures thereof; and wherein the selectivity of said propionic acid is less than about 5 mol % over said TOS of about 72 h. In another embodiment of the present invention, said acrylic acid, acrylic acid derivatives, or mixtures thereof are produced with a yield of at least about 30 mol % and with a selectivity of at least about 70 mol % over a TOS of about 72 h; wherein propionic acid is produced as an impurity along with said acrylic acid, acrylic acid derivatives, or mixtures thereof; and wherein the selectivity of said propionic acid is less than about 1 mol % over said TOS of about 72 h.

In one embodiment of the present invention, said acrylic acid, acrylic acid derivatives, or mixtures thereof are produced with a conversion of said hydroxypropionic acid, hydroxypropionic acid derivatives, or mixtures thereof of more than about 50 mol %. In another embodiment of the present invention, said acrylic acid, acrylic acid derivatives, or mixtures thereof are produced with a conversion of said hydroxypropionic acid, hydroxypropionic acid derivatives, or mixtures thereof of more than about 80 mol %. In yet another embodiment of the present invention, said acrylic acid, acrylic acid derivatives, or mixtures thereof are produced with a conversion of said hydroxypropionic acid, hydroxypropionic acid derivatives, or mixtures thereof of more than about 90 mol %.

In one embodiment of the present invention, acetic acid, pyruvic acid, 1,2-propanediol, hydroxyacetone, acrylic acid dimer, and 2,3-pentanedione are produced along with said acrylic acid, acrylic acid derivatives, or mixtures thereof with a yield of less than about 2 mol % each. In another embodiment of the present invention, acetic acid, pyruvic acid, 1,2-propanediol, hydroxyacetone, acrylic acid dimer, and 2,3-pentanedione are produced along with said acrylic acid, acrylic acid derivatives, or mixtures thereof with a yield of less than about 0.5 mol % each. In yet another embodiment of the present invention, acetaldehyde is produced along with said acrylic acid, acrylic acid derivatives, or mixtures thereof with a yield of less than about 8 mol %. In even yet another embodiment of the present invention, acetaldehyde is produced along with said acrylic acid, acrylic acid derivatives, or mixtures thereof with a yield of less than about 4 mol %. In one embodiment of the present invention, acetaldehyde is produced along with said acrylic acid, acrylic acid derivatives, or mixtures thereof with a yield of less than about 3 mol %.

The feed stream can be introduced into the reactor with a simple tube or through atomization nozzles. Non-limiting examples of atomization nozzles comprise fan nozzles, pressure swirl atomizers, air blast atomizers, two-fluid atomizers, rotary atomizers, and supercritical carbon dioxide atomizers. In one embodiment of the present invention, the droplets of the feed stream are less than about 2 mm in diameter. In another embodiment of the present invention, the droplets of the feed stream are less than about 500 μm in diameter. In yet another embodiment of the present invention, the droplets of the feed stream are less than about 200 μm in diameter. In even yet another embodiment of the present invention, the droplets of the feed stream are less than about 100 μm in diameter.

The product stream can be delivered out of the molten salt catalyst via a variety of methods. Non-limiting examples of methods of delivering the product stream out of the molten salt catalyst are evaporation, dilution, vacuum distillation, steam distillation, and gas stripping. Inert gases or carrier gases can be used in gas stripping. Non-limiting examples as strip gases are air, nitrogen, argon, carbon monoxide, carbon dioxide, and acetaldehyde. In one embodiment of the present invention, said contacting proceeds in the presence of a strip gas. In another embodiment of the present invention, said strip gas is selected from the group consisting of air, nitrogen, argon, carbon monoxide, and mixtures thereof.

The product stream produced in said dehydration is cooled to give a liquid acrylic acid stream as the product stream. The time required to cool the acrylic acid stream must be controlled to reduce acrylic acid polymerization. In one embodiment of the present invention, the residence time of the product stream in the cooling step is less than about 30 s. In another embodiment of the present invention, the residence time of the product stream in the cooling step is between about 0.1 s and about 60 s.

The product stream comprising acrylic acid, acrylic acid derivatives, or mixtures thereof produced according to the present invention can be purified using some or all of the processes of extraction, drying, distilling, cooling, partial melting, and decanting described in US20130274518A1 (incorporated herein by reference) to produce crude and glacial acrylic acid. After purification, the crude and glacial acrylic acid can be polymerized to produce a superabsorbent polymer using processes that are similar to those described in US20130274697A1 (incorporated herein by reference).

In one embodiment of the present invention, a method of making acrylic acid, acrylic acid derivatives, or mixtures thereof comprises contacting a feed stream comprising lactic acid, lactic acid derivatives, or mixtures thereof with a molten salt catalyst in a reactor at a temperature; wherein said molten salt catalyst comprises an IL and an acid; and whereby acrylic acid, acrylic acid derivatives, or mixtures thereof are produced as a result of said dehydration in said reactor. In another embodiment of the present invention, the lactic acid derivative is 2-APA; the IL is [PBu$_4$]Br and the acid is $H_4P_2O_7$; the molar ratio of the IL to the acid is about 4.75; the temperature is about 220° C.; and the acrylic acid is produced with a yield of at least about 10 mol %. In yet another embodiment of the present invention, the lactic acid derivative is lactide; the IL is [PBu$_4$]Br and the acid is $H_4P_2O_7$; the molar ratio of said IL to said acid is about 4.75; the temperature is about 220° C.; and the acrylic acid is produced with a yield of at least about 10 mol %.

In one embodiment of the present invention, a method of making acrylic acid comprises contacting a feed stream comprising 2-APA with a molten salt catalyst in a reactor at 220° C., the molten salt catalyst comprises [PBu$_4$]Br and $H_4P_2O_7$ at a molar ratio of about 4.75, the contacting proceeds under atmospheric pressure and in the presence of a strip gas; the strip gas is argon, and the acrylic acid is produced as a result of the contacting in the reactor with a yield of at least about 30 mol %.

In another embodiment of the present invention, a method of making acrylic acid comprises contacting a feed stream comprising 2-APA with a molten salt catalyst in a reactor at 220° C., the molten salt catalyst comprises [PBu$_4$]Br and HBr at a molar ratio of about 4.75, the contacting proceeds under atmospheric pressure, and the acrylic acid is produced as a result of the contacting in the reactor with a yield of at least about 18 mol %.

In yet another embodiment of the present invention, a method for making acrylic acid, comprises contacting a feed stream comprising 2-APA with a molten salt catalyst in a reactor at 220° C., the molten salt catalyst comprises ethyltriphenylphosphonium bromide ([EtPPh$_3$]Br) and HBr at a molar ratio of about 4, the contacting proceeds under atmospheric pressure, and the acrylic acid is produced as a result of the contacting in the reactor with a yield of at least about 25 mol %.

In even yet another embodiment of the present invention, a method for making acrylic acid, comprises contacting a feed stream comprising lactide with a molten salt catalyst in a reactor at 150° C., the molten salt catalyst comprises tetrabutylphosphonum bromide ([PBu$_4$]Br) and 2-bromopropionic acid (2-BrPA) at a molar ratio of about 10, the contacting proceeds under atmospheric pressure, and the acrylic acid is produced as a result of the contacting in the reactor with a yield of at least about 47 mol %.

In one embodiment of the present invention, a method for making acrylic acid, comprises contacting a feed stream comprising lactide with a molten salt catalyst in a reactor at 150° C., the molten salt catalyst comprises tetrabutylphosphonum bromide ([PBu$_4$]Br) and 2-bromopropionic acid (2-BrPA) at a molar ratio of about 20, the contacting proceeds under atmospheric pressure, and the acrylic acid is produced as a result of the contacting in the reactor with a yield of at least about 52 mol %.

In one embodiment of the present invention, the method of making acrylic acid, acrylic acid derivatives, or mixtures thereof is a one-step process; wherein the feed stream to the one-step process is lactic acid, lactic acid derivatives, or mixtures thereof; and wherein the output stream from the one-step process is acrylic acid, acrylic acid derivatives, or mixtures thereof. In another embodiment of the present invention, the feed stream to the one-step process is lactide and the output stream from the one-step process is acrylic acid.

In yet another embodiment of the present invention, the method of making acrylic acid, acrylic acid derivatives, or mixtures thereof is a two-step process; wherein the feed stream to the first step of the two-step process is lactic acid, lactic acid derivatives, or mixtures thereof; wherein the output stream from the first step and the feed stream to the second step of the two-step process is 2-bromopropionic acid (2-BrPA); and wherein the output stream from the second step of the two-step process is acrylic acid, acrylic acid derivatives, or mixtures thereof. In even yet another embodiment of the present invention, the feed stream to the first step of the two-step process is lactide, and the output stream from the second step of the two-step process is acrylic acid.

In one embodiment of the present invention, the method of making acrylic acid is a two-step process; wherein the feed stream to the first step of the two-step process is lactide; wherein said first step comprises contacting said lactide with 3-methyl-1-(4-butane sulfonic acid) imidazolium bromide ([MIMBS]Br) for about 5 h at a temperature of about 120° C. and atmospheric pressure; whereby 2-bromopropionic acid (2-BrPA) is produced at a yield of more than about 60 mol % and selectivity of more than about 95 mol %; wherein said 2-BrPA is fed into the second step; wherein said second step comprises contacting said 2-BrPA with [PBu$_4$]Br for about 3 h at a temperature of about 160° C. and atmospheric pressure; and whereby acrylic acid is produced at a yield of more than about 45 mol % and selectivity of more than about 85 mol %.

In another embodiment of the present invention, the method of making acrylic acid, acrylic acid derivatives, or mixtures thereof is a three-step process; wherein the feed stream to the first step of the three-step process is lactic acid, lactic acid derivatives, or mixtures thereof; wherein the output stream from the first step and the feed stream to the second step of the three-step process is 2-bromopropionic acid (2-BrPA); wherein the output stream from the second step and the feed stream to the third step of the three-step process is 3-bromopropionic acid (3-BrPA); and wherein the output stream from the third step of the three-step process is acrylic acid, acrylic acid derivatives, or mixtures thereof. In yet another embodiment of the present invention, the feed stream to the first step of the three-step process is lactide, and the output stream from the third step of the three-step process is acrylic acid.

In even yet another embodiment of the present invention, the method of making acrylic acid is a three-step process; wherein the feed stream to the first step of the three-step process is lactide; wherein said first step comprises contacting said lactide with 3-methyl-1-(4-butane sulfonic acid) imidazolium bromide ([MIMBS]Br) for about 5 h at a temperature of about 120° C. and atmospheric pressure; whereby 2-bromopropionic acid (2-BrPA) is produced at a yield of more than about 60 mol % and selectivity of more than about 95 mol %; wherein said 2-BrPA is fed into the second step; wherein said second step comprises contacting said 2-BrPA with [PBu$_4$]Br for about 20 h at a temperature of about 160° C. and atmospheric pressure; whereby 3-bromopropionic acid (3-BrPA) is produced at a yield of more than about 80 mol % and selectivity of more than about 90 mol %; wherein said 3-BrPA is fed into the third step; wherein said third step comprises contacting said 3-BrPA with trioctylamine (TOA) for about 30 min at a temperature of about 180° C. and atmospheric pressure; and whereby acrylic acid is produced at a yield of more than about 90 mol % and selectivity of more than about 90 mol %.

In one embodiment of the present invention, the feed stream comprises lactide. In another embodiment of the present invention, the molten salt catalyst comprises [PBu$_4$]Br and 2-BrPA. In yet another embodiment of the present invention, the temperature in the reactor is between about 110° C. and about 240° C. In even yet another embodiment of the present invention, the temperature in the reactor is between about 130° C. and about 230° C. In one embodiment of the present invention, the temperature in the reactor is between about 150° C. and about 220° C. In another embodiment of the present invention, the temperature in the reactor is between about 160° C. and about 190° C. In yet another embodiment of the present invention, the temperature in the reactor is about 150° C. In even yet another embodiment of the present invention, the temperature in the reactor is about 170° C.

In one embodiment of the present invention, the residence time of the feed stream in the reactor is between about 5 min and about 10 days. In another embodiment of the present invention, the residence time of the feed stream in the reactor is between about 15 min and about 7 days (168 h).

In yet another embodiment of the present invention, the residence time of the feed stream in the reactor is between about 30 min and about 3 days (72 h). In even yet another embodiment of the present invention, the residence time of the feed stream in the reactor is between about 1 h and about 2 days (48 h). In one embodiment of the present invention, the residence time of the feed stream in the reactor is between about 2 h and about 1 day (24 h). In another embodiment of the present invention, the residence time of the feed stream in the reactor is about 0.33 h. In yet another embodiment of the present invention, the residence time of the feed stream in the reactor is about 2 h. In even yet another embodiment of the present invention, the residence time of the feed stream in the reactor is about 7 h.

In one embodiment of the present invention, the molar ratio of the lactic acid equivalent (LAe) to [PBu$_4$]Br to 2-BrPA is between about 1:0.2:0.1 and about 1:5:0.1. In another embodiment of the present invention, the molar ratio of the lactic acid equivalent (LAe) to [PBu$_4$]Br to 2-BrPA is between about 1:0.5:0.1 and about 1:2:0.1. In one embodiment of the present invention, the molar ratio of the lactic acid equivalent (LAe) to [PBu$_4$]Br to 2-BrPA is about 1:1:0.1. In yet another embodiment of the present invention, the molar ratio of the lactic acid equivalent (LAe) to [PBu$_4$]Br to 2-BrPA is about 1:2:0.1.

In one embodiment of the present invention, the molar ratio of the lactic acid equivalent (LAe) to [PBu$_4$]Br is between about 1:0.25 and about 1:4. In another embodiment of the present invention, the molar ratio of the lactic acid equivalent (LAe) to [PBu$_4$]Br is between about 1:0.33 and about 1:3. In yet another embodiment of the present invention, the molar ratio of the lactic acid equivalent (LAe) to [PBu$_4$]Br is between about 1:0.5 and about 1:2. In even yet another embodiment of the present invention, the molar ratio of the lactic acid equivalent (LAe) to [PBu$_4$]Br is about 1:1. In one embodiment of the present invention, the molar ratio of the lactic acid equivalent (LAe) to [PBu$_4$]Br is about 1:2.

In one embodiment of the present invention, the acrylic acid produced in the reactor is removed from the reactor as it is produced. In another embodiment of the present invention, the acrylic acid is removed from the reactor via distillation. In yet another embodiment of the present invention, the acrylic acid is removed with the use of a strip gas.

In one embodiment of the present invention, the water is removed from the reactor as it is introduced into the reactor or produced in the reactor. In another embodiment of the present invention, the water is removed from the reactor via distillation. In yet another embodiment of the present invention, the water is removed with the use of a strip gas.

In one embodiment of the present invention, the feed stream comprises lactic acid and water, and the water is removed from the reactor. In another embodiment of the present invention, the feed stream comprises lactic acid oligomers. In yet another embodiment of the present invention, the feed stream comprises lactic acid and water, and the lactic acid oligomers are formed in the reactor. In even yet another embodiment of the present invention, the feed stream comprises lactic acid and water, and the lactic acid oligomers and acrylic acid are produced simultaneously in the reactor. In one embodiment of the present invention, the feed stream comprises lactic acid and water, the lactic acid oligomers and acrylic acid are produced simultaneously in the reactor, and the water produced is removed from the reactor simultaneously with the production of the lactic acid oligomers and acrylic acid.

In another embodiment of the present invention, the feed stream comprises lactic acid and water, and the lactide and acrylic acid are produced simultaneously in the reactor. In yet another embodiment of the present invention, the feed stream comprises lactic acid and water, the lactide and acrylic acid are produced simultaneously in the reactor, and the water produced is removed from the reactor simultaneously with the production of the lactide and acrylic acid. In even yet another embodiment of the present invention, the feed stream comprises lactic acid and water, the lactide and acrylic acid are produced simultaneously in the reactor, and the acrylic acid and water produced are removed from the reactor simultaneously with the production of the lactide.

In one embodiment of the present invention, the feed stream comprises lactide, the molten salt catalyst comprises [PBu$_4$]Br and 2-BrPA, the molar ratio of lactic acid equivalent to [PBu$_4$]Br to 2-BrPA is about 1:2:01, the reaction temperature is about 160° C., the reaction time is about 24 h, and acrylic acid is produced at a yield of about 58 mol %. In another embodiment of the present invention, the feed stream comprises lactide, the molten salt catalyst comprises [PBu$_4$]Br and 2-BrPA, the molar ratio of lactic acid equivalent to [PBu$_4$]Br to 2-BrPA is about 1:2:01, the reaction temperature is about 160° C., the reaction time is about 24 h, the acrylic acid produced is removed from the reactor as it is produced, and acrylic acid is produced at a yield exceeding about 58 mol %. In yet another embodiment of the present invention, the feed stream comprises lactide, the molten salt catalyst comprises [PBu$_4$]Br and 2-BrPA, the molar ratio of lactic acid equivalent to [PBu$_4$]Br to 2-BrPA is about 1:2:01, the reaction temperature is about 160° C., the reaction time is about 24 h, the acrylic acid produced is removed from the reactor as it is produced, and acrylic acid is produced at a yield exceeding about 70 mol %. In even yet another embodiment of the present invention, the feed stream comprises lactide, the molten salt catalyst comprises [PBu$_4$]Br and 2-BrPA, the molar ratio of lactic acid equivalent to [PBu$_4$]Br to 2-BrPA is about 1:2:01, the reaction temperature is about 160° C., the reaction time is about 24 h, the acrylic acid produced is removed from the reactor as it is produced, and acrylic acid is produced at a yield exceeding about 80 mol %.

In one embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 170° C., the reaction time is about 7 h, and acrylic acid is produced at a yield of about 56 mol %. In another embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 170° C., the reaction time is about 7 h, the acrylic acid produced is removed from the reactor as it is produced, and acrylic acid is produced at a yield exceeding about 56 mol %. In yet another embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 170° C., the reaction time is about 7 h, the acrylic acid produced is removed from the reactor as it is produced, and acrylic acid is produced at a yield exceeding about 70 mol %. In even yet another embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 170° C., the reaction time is about 7 h, the acrylic acid produced is removed from the reactor as it is produced, and acrylic acid is produced at a yield exceeding about 80 mol %.

In one embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 190° C., the reaction time is about 2 h, and acrylic acid is produced at a yield of about 54 mol %. In another embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 190° C., the reaction time is about 2 h, the acrylic acid produced is removed from the reactor as it is produced, and acrylic acid is produced at a yield exceeding about 54 mol %. In yet another embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 190° C., the reaction time is about 2 h, the acrylic acid produced is removed from the reactor as it is produced, and acrylic acid is produced at a yield exceeding about 70 mol %. In even yet another embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 190° C., the reaction time is about 2 h, the acrylic acid produced is removed from the reactor as it is produced, and acrylic acid is produced at a yield exceeding about 80 mol %.

In one embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 220° C., the reaction time is about 0.33 h, and acrylic acid is produced at a yield of about 50 mol %. In another embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 220° C., the reaction time is about 0.33 h, the acrylic acid produced is removed from the reactor as it is produced, and acrylic acid is produced at a yield exceeding about 50 mol %. In yet another embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 220° C., the reaction time is about 0.33 h, the acrylic acid produced is removed from the reactor as it is produced, and acrylic acid is produced at a yield exceeding about 70 mol %. In even yet another embodiment of the present invention, the molten salt catalyst comprises [PBu$_4$]Br and 2-BrPA, the molar ratio of lactic acid equivalent to [PBu$_4$]Br to 2-BrPA is about 1:2:01, the reaction temperature is about 220° C., the reaction time is about 0.33 h, the acrylic acid produced is removed from the reactor as it is produced, and acrylic acid is produced at a yield exceeding about 80 mol %.

In one embodiment of the present invention, the water content of the reaction mixture is more than about 1 wt %. In another embodiment of the present invention, the water content of the reaction mixture is more than about 2 wt %. In yet another embodiment of the present invention, the water content of the reaction mixture is more than about 3 wt %. In even yet another embodiment of the present invention, the water content of the reaction mixture is about 1 wt % or less.

IV Examples

The following examples are provided to illustrate the invention, but are not intended to limit the scope thereof.

Example 1—Acrylic Acid Synthesis from 2-APA with [PBu$_4$]Br Ionic Liquid, Molar Ratio of Lactic Acid Equivalent (LAe) to [PBu$_4$]Br Equal to 2.57:1, Temperature 220° C., and No Strip Gas 18 g of solid tetrabutylphosphonium bromide salt catalyst ([PBu$_4$]Br; 51.99 mmol, 98%; Sigma-Aldrich Chemie GmbH, Taufkirchen, Germany; catalog #189138) were placed in a 100 mL three-necked glass reactor at room temperature and atmospheric conditions, and then heated to 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed using a water-cooled condenser. The liquid products were collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 1.3 mol % and a 2-APA conversion of ≥97 mol %.

Example 2—Acrylic Acid Synthesis from 2-APA with [PBu$_4$]Br and H$_4$P$_2$O$_7$ Molten Salt Catalyst, Molar Ratio of Lactic Acid Equivalent (LAe) to [PBu$_4$]Br to H$_4$P$_2$O$_7$ Equal to 71.8:28:1, Temperature 220° C., and No Strip Gas The molten salt catalyst with a molar ratio of 28 was prepared by first mixing 0.37 g of solid pyrophosphoric acid (H$_4$P$_2$O$_7$; 1.86 mmol, ≥90%; Sigma-Aldrich Chemie GmbH, Taufkirchen, Germany; catalog #83210) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 5.5 mol % and a 2-APA conversion of ≥97 mol %.

Example 3—Acrylic Acid Synthesis from 2-APA with [PBu$_4$]Br and H$_4$P$_2$O$_7$ Molten Salt Catalyst, Molar Ratio of Lactic Acid Equivalent (LAe) to [PBu$_4$]Br to H$_4$P$_2$O$_7$ Equal to 36:14:1, Temperature 220° C., and No Strip Gas The molten salt catalyst with a molar ratio of 14 was prepared by first mixing 0.73 g of solid pyrophosphoric acid ($H_4P_2O_7$; 3.71 mmol, ≥90%; Sigma-Aldrich Chemie GmbH, Taufkirchen, Germany; catalog #83210) and 18 g of solid tetrabutylphosphonium bromide ([$PBu_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene ($C_6H_3(CH_3)_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 7.0 mol % and a 2-APA conversion of ≥97 mol %.

Example 4—Acrylic Acid Synthesis from 2-APA with [$PBu_4$]Br and $H_4P_2O_7$ Molten Salt Catalyst, Molar Ratio of Lactic Acid Equivalent (LAe) to [$PBu_4$]Br to $H_4P_2O_7$ Equal to 18:7:1, Temperature 220° C., and No Strip Gas The molten salt catalyst with a molar ratio of 7 was prepared by first mixing 1.47 g of solid pyrophosphoric acid ($H_4P_2O_7$; 7.43 mmol, ≥90%; Sigma-Aldrich Chemie GmbH, Taufkirchen, Germany; catalog #83210) and 18 g of solid tetrabutylphosphonium bromide ([$PBu_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene ($C_6H_3(CH_3)_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 9.6 mol % and a 2-APA conversion of ≥97 mol %.

Example 5—Acrylic Acid Synthesis from 2-APA with [$PBu_4$]Br and $H_4P_2O_7$ Molten Salt Catalyst, Molar Ratio of Lactic Acid Equivalent (LAe) to [$PBu_4$]Br to $H_4P_2O_7$ Equal to 12.2:4.75:1, Temperature 220° C., and No Strip Gas The molten salt catalyst with a molar ratio of 4.75 was prepared by first mixing 2.16 g of solid pyrophosphoric acid ($H_4P_2O_7$; 10.94 mmol, ≥90%; Sigma-Aldrich Chemie GmbH, Taufkirchen, Germany; catalog #83210) and 18 g of solid tetrabutylphosphonium bromide ([$PBu_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene ($C_6H_3(CH_3)_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 11.1 mol % and a 2-APA conversion of ≥97 mol %.

Example 6—Acrylic Acid Synthesis from 2-APA with [$PBu_4$]Br and $H_4P_2O_7$ Molten Salt Catalyst, Molar Ratio of Lactic Acid Equivalent (LAe) to [$PBu_4$]Br to $H_4P_2O_7$ Equal to 9:3.5:1, Temperature 220° C., and No Strip Gas The molten salt catalyst with a molar ratio of 3.5 was prepared by first mixing 2.94 g of solid pyrophosphoric acid ($H_4P_2O_7$; 14.85 mmol, ≥90%; Sigma-Aldrich Chemie GmbH, Taufkirchen, Germany; catalog #83210) and 18 g of solid tetrabutylphosphonium bromide ([$PBu_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene ($C_6H_3(CH_3)_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 8.8 mol % and a 2-APA conversion of ≥97 mol %.

Example 7—Acrylic Acid Synthesis from 2-APA with [$PBu_4$]Br and $H_4P_2O_7$ Molten Salt Catalyst, Molar Ratio of Lactic Acid Equivalent (LAe) to [$PBu_4$]Br to $H_4P_2O_7$ Equal to 2.57:1:1, Temperature 220° C., and No Strip Gas The molten salt catalyst with a molar ratio of 1 was prepared by first mixing 10.28 g of solid pyrophosphoric acid ($H_4P_2O_7$; 51.99 mmol, ≥90%; Sigma-Aldrich Chemie GmbH, Taufkirchen, Germany; catalog #83210) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 1.4 mol % and a 2-APA conversion of ≥97 mol %.

Example 8—Acrylic Acid Synthesis from 2-APA with H$_4$P$_2$O$_7$ Acid, Molar Ratio of Lactic Acid Equivalent (LAe) to H$_4$P$_2$O$_7$ Equal to 1.47:1, Temperature 220° C., and No Strip Gas 18 g of solid pyrophosphoric acid catalyst (H$_4$P$_2$O$_7$; 91.02 mmol, ≥90%; Sigma-Aldrich Chemie GmbH, Taufkirchen, Germany; catalog #83210) were placed in a 100 mL three-necked glass reactor at room temperature and atmospheric conditions, and then heated to 220° C. under continuous stirring with an overhead stirrer at a speed of 300 rpm. After the catalyst reached 220° C., 17.64 g (133.5 mmol) of synthesized pure 2-APA were fed into the glass reactor at a constant feeding rate of 0.5 mL/min by means of a funnel. Uncontrollable foaming was observed in the glass reactor that yielded in no distillate and thus the yield of acrylic acid was 0 mol %.

Example 9—Acrylic Acid Synthesis from 2-APA with [PBu$_4$]Br and KBr Molten Salt Catalyst, Molar Ratio of Lactic Acid Equivalent (LAe) to [PBu$_4$]Br to KBr Equal to 12.2:4.75:1, Temperature 220° C., and No Strip Gas The molten salt catalyst with a molar ratio of 4.75 was prepared by first mixing 1.32 g of solid potassium bromide (KBr; 10.94 mmol, 99%; Sigma-Aldrich Chemie GmbH, Taufkirchen, Germany; catalog # P0838) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 0.7 mol %.

Example 10—Acrylic Acid Synthesis from 2-APA with [PBu$_4$]Br and CaBr$_2$ Molten Salt Catalyst, Molar Ratio of Lactic Acid Equivalent (LAe) to [PBu$_4$]Br to CaBr$_2$ Equal to 12.2:4.75:1, Temperature 220° C., and No Strip Gas The molten salt catalyst with a molar ratio of 4.75 was prepared by first mixing 2.23 g of solid calcium bromide (CaBr$_2$; 10.94 mmol, 98%; Sigma-Aldrich Chemie GmbH, Taufkirchen, Germany; catalog #233749) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 11.8 mol % and a 2-APA conversion of ≥97 mol %.

Example 11—Acrylic Acid Synthesis from 2-APA with [PBu$_4$]Br and MgBr$_2$ Molten Salt Catalyst, Molar Ratio of Lactic Acid Equivalent (LAe) to [PBu$_4$]Br to MgBr$_2$ Equal to 12.2:4.75:1, Temperature 220° C., and No Strip Gas The molten salt catalyst with a molar ratio of 4.75 was prepared by first mixing 2.06 g of solid magnesium bromide (MgBr$_2$; 10.94 mmol, ≥98%; Sigma-Aldrich Chemie GmbH, Taufkirchen, Germany; catalog #360074) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 12.9 mol % and a 2-APA conversion of ≥97 mol %.

Example 12—Acrylic Acid Synthesis from 2-APA with [PBu$_4$]Br and AlBr$_3$ Molten Salt Catalyst, Molar Ratio of Lactic Acid Equivalent (LAe) to [PBu$_4$]Br to AlBr$_3$ Equal to 12.2:4.75:1, Temperature 220° C., and No Strip Gas The molten salt catalyst with a molar ratio of 4.75 was prepared by first mixing 2.98 g of solid aluminum tribromide (AlBr$_3$; 10.94 mmol, ≥98%; Sigma-Aldrich Chemie GmbH, Taufkirchen, Germany; catalog #210072) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 14.3 mol % and a 2-APA conversion of ≥94 mol %.

Example 13—Acrylic Acid Synthesis from 2-APA with [PBu$_4$]Br and InBr$_3$ Molten Salt Catalyst, Molar Ratio of Lactic Acid Equivalent (LAe) to [PBu$_4$]Br to InBr$_3$ Equal to 12.2:4.75:1, Temperature 220° C., and No Strip Gas The molten salt catalyst with a molar ratio of 4.75 was prepared by first mixing 3.92 g of solid indium tribromide (InBr$_3$; 10.94 mmol, ≥99%; Sigma-Aldrich Chemie GmbH, Taufkirchen, Germany; catalog #308285) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 0.8 mol % and a 2-APA conversion of ≥97 mol %.

Example 14—Acrylic Acid Synthesis from 2-APA with [PBu$_4$]Br and NiBr$_2$ Molten Salt Catalyst, Molar Ratio of Lactic Acid Equivalent (LAe) to [PBu$_4$]Br to NiBr$_2$ Equal to 12.2:4.75:1, Temperature 220° C., and No Strip Gas The molten salt catalyst with a molar ratio of 4.75 was prepared by first mixing 2.44 g of solid Nickel dibromide (NiBr$_2$; 10.94 mmol, 98%; Sigma-Aldrich Chemie GmbH, Taufkirchen, Germany; catalog #217891) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 0.5 mol %.

Example 15—Acrylic Acid Synthesis from 2-APA with [PBu$_4$]Br and CoBr$_2$ Molten Salt Catalyst, Molar Ratio of Lactic Acid Equivalent (LAe) to [PBu$_4$]Br to CoBr$_2$ Equal to 12.2:4.75:1, Temperature 220° C., and No Strip Gas The molten salt catalyst with a molar ratio of 4.75 was prepared by first mixing 2.42 g of solid cobalt dibromide (CoBr$_2$; 10.94 mmol, 99%; Sigma-Aldrich Chemie GmbH, Taufkirchen, Germany; catalog #334022) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 0.6 mol %.

Example 16—Acrylic Acid Synthesis from 2-APA with [PBu$_4$]Br and ZnBr$_2$ Molten Salt Catalyst, Molar Ratio of Lactic Acid Equivalent (LAe) to [PBu$_4$]Br to ZnBr$_2$ Equal to 12.2:4.75:1, Temperature 220° C., and No Strip Gas The molten salt catalyst with a molar ratio of 4.75 was prepared by first mixing 2.47 g of solid zinc dibromide (ZnBr$_2$; 10.94 mmol, 99.999%; Sigma-Aldrich Chemie GmbH, Taufkirchen, Germany; catalog #230022) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 0.7 mol %.

Example 17—Acrylic Acid Synthesis from 2-APA with [PBu$_4$]Br and FeBr$_3$ Molten Salt Catalyst, Molar Ratio of Lactic Acid Equivalent (LAe) to [PBu$_4$]Br to FeBr$_3$ Equal to 12.2:4.75:1, Temperature 220° C., and No Strip Gas The molten salt catalyst with a molar ratio of 4.75 was prepared by first mixing 3.30 g of solid iron tribromide (FeBr$_3$; 10.94 mmol, 98%; Sigma-Aldrich Chemie GmbH, Taufkirchen, Germany; catalog #217883) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 1.0 mol %.

Example 18—Acrylic Acid Synthesis from 2-APA with [PBu$_4$]Br and GaBr$_3$ Molten Salt Catalyst, Molar Ratio of Lactic Acid Equivalent (LAe) to [PBu$_4$]Br to GaBr$_3$ Equal to 14.95:4.75:1, Temperature 220° C., and No Strip Gas The molten salt catalyst with a molar ratio of 4.75 was prepared by first mixing 2.76 g of solid gallium tribromide (GaBr$_3$; 8.93 mmol, 99.999%; Sigma-Aldrich Chemie GmbH, Taufkirchen, Germany; catalog #381357) and 14.69 g of solid tetrabutylphosphonium bromide ([PBu$_4$]Br; 42.43 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 1.2 mol %.

Example 19—Acrylic Acid Synthesis from 2-APA with [PBu$_4$]Br and CuBr$_2$ Molten Salt Catalyst, Molar Ratio of Lactic Acid Equivalent (LAe) to [PBu$_4$]Br to CuBr$_2$ Equal to 12.2:4.75:1, Temperature 220° C., and No Strip Gas The molten salt catalyst with a molar ratio of 4.75 was prepared by first mixing 2.47 g of solid copper dibromide (CuBr$_2$; 10.94 mmol, 99%; Sigma-Aldrich Chemie GmbH, Taufkirchen, Germany; catalog #221775) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 8.2 mol % and a 2-APA conversion of ≥90 mol %.

Example 20—Acrylic Acid Synthesis from 2-APA with [PBu$_4$]Br and HBr/AlBr$_3$ Molten Salt Catalyst, Molar Ratio of Lactic Acid Equivalent (LAe) to [PBu$_4$]Br to HBr/AlBr$_3$ Equal to 12.2:4.75:1, Temperature 220° C., and No Strip Gas The molten salt catalyst with a molar ratio of 4.75 was prepared by first mixing 2.98 g of solid aluminum tribromide (AlBr$_3$; 10.94 mmol, ≥98%; Sigma-Aldrich Chemie GmbH, Taufkirchen, Germany; catalog #210072), 1.88 g of liquid hydrobromic acid (HBr; 10.94 mmol, 47%; Merck KGaA, Darmstadt, Germany; catalog #1.00304.0500) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 9.9 mol % and a 2-APA conversion of ≥93 mol %.

Example 21—Acrylic Acid Synthesis from 2-APA with [PBu$_4$]Br and Acetic Acid (CH$_3$CO$_2$H) Molten Salt Catalyst, Molar Ratio of Lactic Acid Equivalent (LAe) to [PBu$_4$]Br to Acetic Acid Equal to 12.2:4.75:1, Temperature 220° C., and No Strip Gas The molten salt catalyst with a molar ratio of 4.75 was prepared by first mixing 0.67 g of liquid acetic acid (acetic acid; 11.16 mmol, 100%; Merck Schuchardt OHG, Hohenbrunn, Germany; catalog #100063) and 18 g of solid tetrabutylphosphonium bromide ([PBu$_4$]Br; 51.99 mmol, 99%; Alfa Aesar, Karlsruhe, Germany; catalog # A10868) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a hose pump. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 3.4 mol % and a 2-APA conversion of ≥97 mol %.

Example 22—Acrylic Acid Synthesis from 2-APA with [PBu$_4$]Br and H$_3$PO$_4$ Molten Salt Catalyst, Molar Ratio of Lactic Acid Equivalent (LAe) to [PBu$_4$]Br to H$_3$PO$_4$ Equal to 12.2:4.75:1, Temperature 220° C., and No Strip Gas The molten salt catalyst with a molar ratio of 4.75 was prepared by first mixing 1.26 g of liquid phosphoric acid (H$_3$PO$_4$; 10.94 mmol, 85%; Merck KGaA, Darmstadt, Germany; catalog #1.00573.1000) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 6.2 mol % and a 2-APA conversion of ≥97 mol %.

Example 23—Acrylic Acid Synthesis from 2-APA with [PBu$_4$]Br and H$_2$SO$_4$ Molten Salt Catalyst, Molar Ratio of Lactic Acid Equivalent (LAe) to [PBu$_4$]Br to H$_2$SO$_4$ Equal to 12.2:4.75:1, Temperature 220° C., and No Strip Gas The molten salt catalyst with a molar ratio of 4.75 was prepared by first mixing 2.15 g of liquid sulfuric acid (H$_2$SO$_4$; 10.94 mmol, 50%; PanReac AppliChem, Darmstadt, Germany; catalog #A2102,2500) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 11.8 mol % and a 2-APA conversion of ≥97 mol %.

Example 24—Acrylic Acid Synthesis from 2-APA with [PBu$_4$]Br and HBr Molten Salt Catalyst, Molar Ratio of Lactic Acid Equivalent (LAe) to [PBu$_4$]Br to HBr Equal to 51.4:20:1, Temperature 220° C., and No Strip Gas The molten salt catalyst with a molar ratio of 20 was prepared by first mixing 0.45 g of liquid hydrobromic acid (HBr; 2.61 mmol, 47%; Merck KGaA, Darmstadt, Germany; catalog #1.00304.0500) and 18.01 g of solid tetrabutylphosphonium bromide ([PBu$_4$]Br; 52.01 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.72 g (134.1 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 7.3 mol % and a 2-APA conversion of ≥97 mol %.

Example 25—Acrylic Acid Synthesis from 2-APA with [PBu$_4$]Br and HBr Molten Salt Catalyst, Molar Ratio of Lactic Acid Equivalent (LAe) to [PBu$_4$]Br to HBr Equal to 25.7:10:1, Temperature 220° C., and No Strip Gas The molten salt catalyst with a molar ratio of 10 was prepared by first mixing 0.90 g of liquid hydrobromic acid (HBr; 5.23 mmol, 47%; Merck KGaA, Darmstadt, Germany; catalog #1.00304.0500) and 18.02 g of solid tetrabutylphosphonium bromide ([PBu$_4$]Br; 52.04 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.78 g (134.6 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 13 mol % and a 2-APA conversion of ≥97 mol %.

Example 26—Acrylic Acid Synthesis from 2-APA with [PBu$_4$]Br and HBr Molten Salt Catalyst, Molar Ratio of Lactic Acid Equivalent (LAe) to [PBu$_4$]Br to HBr Equal to 15.7:6:1, Temperature 220° C., and No Strip Gas The molten salt catalyst with a molar ratio of 6 was prepared by first mixing 1.47 g of liquid hydrobromic acid (HBr; 8.54 mmol, 47%; Merck KGaA, Darmstadt, Germany; catalog #1.00304.0500) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.66 g (133.7 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 14.3 mol % and a 2-APA conversion of ≥97 mol %.

Example 27a—Acrylic Acid Synthesis from 2-APA with [PBu$_4$]Br and HBr Molten Salt Catalyst, Molar Ratio of Lactic Acid Equivalent (LAe) to [PBu$_4$]Br to HBr Equal to 12.2:4.75:1, Temperature 220° C., and No Strip Gas The molten salt catalyst with a molar ratio of 4.75 was prepared by first mixing 1.88 g of liquid hydrobromic acid (HBr; 10.94 mmol, 47%; Merck KGaA, Darmstadt, Germany; catalog #1.00304.0500) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 18.4 mol % and a 2-APA conversion of ≥97 mol %.

Example 27b—Acrylic Acid Synthesis from 2-APA with [PBu$_4$]Br and HBr Molten Salt Catalyst, Molar Ratio of Lactic Acid Equivalent (LAe) to [PBu$_4$]Br to HBr Equal to 12.2:4.75:1, Temperature 160° C., and No Strip Gas The molten salt catalyst with a molar ratio of 4.75 was prepared by first mixing 1.88 g of liquid hydrobromic acid (HBr; 10.94 mmol, 47%; Merck KGaA, Darmstadt, Germany; catalog #1.00304.0500) and 18 g of solid tetrabutylphosphonium bromide ([PBu$_4$]Br; 51.99 mmol, 99%; Alfa Aesar, Karlsruhe, Germany; catalog # A10868) at room temperature and atmospheric conditions in a 100 mL three-necked glass reactor, and then heating the catalyst at a temperature of 160° C. under continuous stirring with an overhead stirrer at a speed of 300 rpm. After the molten salt catalyst reached a constant temperature of 160° C., 17.64 g (133.5 mmol) of synthesized pure 2-APA were fed into the glass reactor at a constant feeding rate of 0.2 mL/min by means of a hose pump. The 2-APA was slowly dropped into the glass reactor. No reaction products were semi-batchwise removed due to the low reaction temperature of 160° C. The gaseous by-products were routed to the off-gas. After an overall process time of 150 min the reaction flask was analyzed via off-line $^1$H NMR (JEOL ECX 400 MHz). $^1$H qNMR analysis of the reaction mixture gave an acrylic acid yield of about 1 mol % and a 2-APA conversion of 66.8 mol %.

Example 27c—Acrylic Acid Synthesis from 2-APA with [PBu$_4$]Br and HBr Molten Salt Catalyst, Molar Ratio of Lactic Acid Equivalent (LAe) to [PBu$_4$]Br to HBr Equal to 12.2:4.75:1, Temperature 180° C., and No Strip Gas The molten salt catalyst with a molar ratio of 4.75 was prepared by first mixing 1.88 g of liquid hydrobromic acid (HBr; 10.94 mmol, 47%; Merck KGaA, Darmstadt, Germany; catalog #1.00304.0500) and 18 g of solid tetrabutylphosphonium bromide ([PBu$_4$]Br; 51.99 mmol, 99%; Alfa Aesar, Karlsruhe, Germany; catalog # A10868) at room temperature and atmospheric conditions in a 100 mL three-necked glass reactor, and then heating the catalyst at a temperature of 180° C. under continuous stirring with an overhead stirrer at a speed of 300 rpm. After the molten salt catalyst reached a constant temperature of 180° C., 17.64 g (133.5 mmol) of synthesized pure 2-APA were fed into the glass reactor at a constant feeding rate of 0.2 mL/min by means of a hose pump. The 2-APA was slowly dropped into the glass reactor. No reaction products were semi-batchwise removed due to the low reaction temperature of 180° C. The gaseous by-products were routed to the off-gas. After an overall process time of 150 min the reaction flask was analyzed via off-line $^1$H NMR (JEOL ECX 400 MHz). $^1$H qNMR analysis of the reaction mixture gave an acrylic acid yield of about 1 mol % and a 2-APA conversion of 67.0 mol %.

Example 28—Acrylic Acid Synthesis from 2-APA with [PBu$_4$]Br and HBr Molten Salt Catalyst, Molar Ratio of Lactic Acid Equivalent (LAe) to [PBu$_4$]Br to HBr Equal to 10.3:4:1, Temperature 220° C., and No Strip Gas The molten salt catalyst with a molar ratio of 4 was prepared by first mixing 2.23 g of liquid hydrobromic acid (HBr; 12.95 mmol, 47%; Merck KGaA, Darmstadt, Germany; catalog #1.00304.0500) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.68 g (133.8 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 18.5 mol % and a 2-APA conversion of ≥97 mol %.

Example 29—Acrylic Acid Synthesis from 2-APA with [PBu$_4$]Br and HBr Molten Salt Catalyst, Molar Ratio of Lactic Acid Equivalent (LAe) to [PBu$_4$]Br to HBr Equal to 5.1:2:1, Temperature 220° C., and No Strip Gas The molten salt catalyst with a molar ratio of 2 was prepared by first mixing 4.47 g of liquid hydrobromic acid (HBr; 25.97 mmol, 47%; Merck KGaA, Darmstadt, Germany; catalog #1.00304.0500) and 18.02 g of solid tetrabutylphosphonium bromide ([PBu$_4$]Br; 52.04 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene (C$_6$H$_3$(CH$_3$)$_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 18.7 mol % and a 2-APA conversion of ≥97 mol %.

Example 30—Acrylic Acid Synthesis from 2-APA with HBr Acid, Molar Ratio of Lactic Acid Equivalent (LAe) to HBr Equal to 10.3:1, and No Strip Gas 2.46 g of liquid hydrobromic acid (HBr; 14.29 mmol, 47%; Merck KGaA, Darmstadt, Germany; catalog #1.00304.0500) were mixed with 19.41 g (146.9 mmol) of synthesized pure 2-APA, placed in a 100 mL three-necked glass reactor at room temperature and atmospheric conditions, and then heated to 220° C. under continuous stirring with an overhead stirrer at a speed of 300 rpm. The liquid products were condensed and collected in an ice-cooled flask, and the gaseous by-products were routed to the off-gas. After an overall process time of 150 min, 1 g of mesitylene ($C_6H_3(CH_3)_3$; 8.15 mmol, 98%; Sigma-Aldrich Chemie GmbH, Taufkirchen, Germany; catalog # M7200) was added to the distillation flask as internal standard and the collected distillate, as well as the residue in the three-necked glass reactor, were both analyzed via off-line $^1$H NMR (JEOL ECX 400 MHz). $^1$H qNMR analysis of the distillate gave an acrylic acid yield of about 0 mol %.

Example 31—Acrylic Acid Synthesis from 2-APA with [PBu$_4$]Br and H$_4$P$_2$O$_7$ Molten Salt Catalyst, Molar Ratio of Lactic Acid Equivalent (LAe) to [PBu$_4$]Br to H$_4$P$_2$O$_7$ Equal to 24.2:4.75:1 Temperature 220° C., and Argon Strip Gas The molten salt catalyst with a molar ratio of 4.75 was prepared by first mixing 4.3 g of solid pyrophosphoric acid (H$_4$P$_2$O$_7$; 21.9 mmol, ≥90%; Sigma-Aldrich Chemie GmbH, Taufkirchen, Germany; catalog #83210) and 36 g of solid tetrabutylphosphonium bromide ([PBu$_4$]Br; 104 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 70 g (530 mmol) of synthesized pure 2-APA were fed into the glass reactor at a constant feeding rate of 0.25 mL/min by means of a hose pump. The 2-APA was slowly dropped into the glass reactor and the reaction products were semi-batchwise removed using a water-cooled condenser and Ar strip gas at 200 mLn/min. The liquid products were condensed and collected in an ice-cooled flask, and the gaseous by-products were routed to the off-gas. After an overall process time of 5 h, 1 g of mesitylene ($C_6H_3(CH_3)_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 32 mol % and a 2-APA conversion of ≥97 mol %.

Example 32—Acrylic Acid Synthesis from 2-APA with [PBu$_4$]Br and H$_4$P$_2$O$_7$ Molten Salt Catalyst, Molar Ratio of Lactic Acid Equivalent (LAe) to [PBu$_4$]Br to H$_4$P$_2$O$_7$ Equal to 17.7:3.5:1, Temperature 220° C., and Argon Strip Gas The molten salt catalyst with a molar ratio of 3.5 was prepared by first mixing 5.9 g of solid pyrophosphoric acid (H$_4$P$_2$O$_7$; 30 mmol, ≥90%; Sigma-Aldrich Chemie GmbH, Taufkirchen, Germany; catalog #83210) and 36 g of solid tetrabutylphosphonium bromide ([PBu$_4$]Br; 104 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 70 g (530 mmol) of synthesized pure 2-APA were fed into the glass reactor at a constant feeding rate of 0.25 mL/min by means of a hose pump. The 2-APA was slowly dropped into the glass reactor and the reaction products were semi-batchwise removed using a water-cooled condenser and Ar strip gas at 200 mLn/min. The liquid products were condensed and collected in an ice-cooled flask, and the gaseous by-products were routed to the off-gas. After an overall process time of 5 h, 1 g of mesitylene ($C_6H_3(CH_3)_3$; 8.15 mmol, 98%; Sigma-Aldrich Chemie GmbH, Taufkirchen, Germany; catalog #M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 23 mol % and a 2-APA conversion of about ≥97 mol %.

Example 33—Acrylic Acid Synthesis from 2-APA with [PBu$_4$]Cl and H$_4$P$_2$O$_7$ Molten Salt Catalyst, Molar Ratio of Lactic Acid Equivalent (LAe) to [PBu$_4$]Cl to H$_4$P$_2$O$_7$ Equal to 10.8:4.75:1, Temperature 220° C., and No Strip Gas The molten salt catalyst with a molar ratio of 4.75 was prepared by first mixing 2.44 g of solid pyrophosphoric acid (H$_4$P$_2$O$_7$; 12.34 mmol, ≥90%; Sigma-Aldrich Chemie GmbH, Taufkirchen, Germany; catalog #83210) and 18 g of solid tetrabutylphosphonium chloride ([PBu$_4$]Cl; 8.6 mmol, 96%; Sigma-Aldrich Chemie GmbH, Taufkirchen, Germany; catalog #144800) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene ($C_6H_3(CH_3)_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of <1 mol %.

Example 34—Acrylic Acid Synthesis from 2-APA with [PBu$_4$]I and H$_4$P$_2$O$_7$ Molten Salt Catalyst, Molar Ratio of Lactic Acid Equivalent (LAe) to [PBu$_4$]I to H$_4$P$_2$O$_7$ Equal to 13.9:4.75:1, Temperature 220° C., and No Strip Gas The molten salt catalyst with a molar ratio of 4.75 was prepared by first mixing 1.9 g of solid pyrophosphoric acid (H$_4$P$_2$O$_7$; 9.61 mmol, ≥90%; Sigma-Aldrich Chemie GmbH, Taufkirchen, Germany; catalog #83210) and 18 g of solid tetrabutylphosphonium iodide ([PBu$_4$]I; 45.66 mmol, 98%; Alfa Aesar GmbH & Co KG, Karlsruhe, Germany; catalog # A16792) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220°

C., 17.64 g (133.5 mmol) of synthesized pure 2-APA were fed into the glass reactor at a constant feeding rate of 0.5 mL/min by means of a funnel. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 1 g of mesitylene ($C_6H_3(CH_3)_3$; 8.15 mmol, 98%; Sigma-Aldrich Chemie GmbH, Taufkirchen, Germany; catalog # M7200) was added to the distillation flask as internal standard and the collected distillate, as well as the molten salt catalyst, were both analyzed via off-line $^1H$ NMR (JEOL ECX 400 MHz). $^1H$ qNMR analysis of the distillate gave an acrylic acid yield of <1 mol %.

Example 35—Acrylic Acid Synthesis from 88 wt % Lactic Acid Aqueous Solution with [PBu$_4$]Br and H$_4$P$_2$O$_7$ Molten Salt Catalyst, Molar Ratio of Lactic Acid Equivalent (LAe) to [PBu$_4$]Br to H$_4$P$_2$O$_7$ Equal to 6.6:3.5:1, Temperature 220° C., and No Strip Gas The molten salt catalyst with a molar ratio of 3.5 was prepared by first mixing 2.90 g of solid pyrophosphoric acid ($H_4P_2O_7$; 14.85 mmol, ≥90%; Sigma-Aldrich Chemie GmbH, Taufkirchen, Germany; catalog #83210) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 10 g of an 88 wt % L-lactic acid solution (Corbion Purac Co., Lenexa, Kans.; 97.8 mmol LAe) were fed into the glass reactor at a constant feeding rate of 0.33 mL/min by means of a funnel. The LA solution was slowly dropped into the glass reactor and the reaction products were semi-batchwise removed. The liquid products were condensed and collected in an ice-cooled flask, and the gaseous by-products were routed to the off-gas. After an overall process time of 150 min, 0.5 g of hydroquinone ($C_6H_4$-1,4-$(OH)_2$; 4.52 mmol, 99.5%; Sigma-Aldrich Chemie GmbH, Taufkirchen, Germany; catalog # H17902) were added to the distillation flask as internal standard and the collected distillate, as well as the molten salt catalyst, were both analyzed via off-line $^1H$ NMR (JEOL ECX 400 MHz). $^1H$ qNMR analysis of the distillate gave an acrylic acid yield of about 4 mol %.

Example 36—Acrylic Acid Synthesis from Lactide with [PBu$_4$]Br and H$_4$P$_2$O$_7$ Molten Salt Catalyst, Molar Ratio of Lactic Acid Equivalent (LAe) to [PBu$_4$]Br to H$_4$P$_2$O$_7$ Equal to 9:3.5:1, Temperature 220° C., and No Strip Gas 10 g of solid lactide ($C_6H_8O_4$; 66.61 mmol, 133.22 mmol LAe, >96%; Sigma-Aldrich Chemie GmbH, Taufkirchen, Germany; catalog #303143) were placed in a 100 mL three-necked glass reactor. The molten salt catalyst with a molar ratio of 3.5 was prepared by mixing 2.90 g of solid pyrophosphoric acid ($H_4P_2O_7$; 14.85 mmol, ≥90%; Sigma-Aldrich Chemie GmbH, Taufkirchen, Germany; catalog #83210) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in the 100 mL three-necked glass reactor, and then heating the catalyst and the reactant at a temperature of 220° C. under continuous stirring with an overhead stirrer at a speed of 300 rpm. While the molten salt catalyst and the reactant were kept at a constant temperature of 220° C. the reaction products were semi-batchwise removed. The liquid products were condensed and collected in an ice-cooled flask, and the gaseous by-products were routed to the off-gas. After an overall process time of 150 min, 0.5 g of hydroquinone ($C_6H_4$-1, 4-$(OH)_2$; 4.52 mmol, 99.5%; Sigma-Aldrich Chemie GmbH, Taufkirchen, Germany; catalog # H17902) were added to the distillation flask as internal standard and the collected distillate, as well as the molten salt catalyst, were both analyzed via off-line $^1H$ NMR (JEOL ECX 400 MHz). $^1H$ qNMR analysis of the distillate gave an acrylic acid yield of about 8.8 mol %.

Example 37—Acrylic Acid Synthesis from ETFP with [PBu$_4$]Br and H$_4$P$_2$O$_7$ Molten Salt Catalyst, Molar Ratio of Lactic Acid Equivalent (LAe) to [PBu$_4$]Br to H$_4$P$_2$O$_7$ Equal to 3.1:3.5:1, Temperature 220° C., and No Strip Gas The molten salt catalyst with a molar ratio of 3.5 was prepared by first mixing 2.90 g of solid pyrophosphoric acid ($H_4P_2O_7$; 14.85 mmol, ≥90%; Sigma-Aldrich Chemie GmbH, Taufkirchen, Germany; catalog #83210) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 10 g (46.7 mmol) of synthesized pure ETFP were fed into the glass reactor at a constant feeding rate of 0.33 mL/min by means of a funnel. The ETFP was slowly dropped into the glass reactor and the reaction products were semi-batchwise removed. The liquid products were condensed and collected in an ice-cooled flask, and the gaseous by-products were routed to the off-gas. After an overall process time of 150 min, 0.5 g of mesitylene ($C_6H_3(CH_3)_3$; 4.08 mmol, 98%; Sigma-Aldrich Chemie GmbH, Taufkirchen, Germany; catalog # M7200) were added to the distillation flask as internal standard and the collected distillate, as well as the molten salt catalyst, were both analyzed via off-line $^1H$ NMR (JEOL ECX 400 MHz). $^1H$ qNMR analysis of the distillate gave an acrylic acid yield of about 15.6 mol %.

Example 38—Acrylic Acid Synthesis from EAPA with [PBu$_4$]Br and H$_4$P$_2$O$_7$ Molten Salt Catalyst, Molar Ratio of Lactic Acid Equivalent (LAe) to [PBu$_4$]Br to H$_4$P$_2$O$_7$ Equal to 4.2:3.5:1, Temperature 220° C., and No Strip Gas The molten salt catalyst with a molar ratio of 3.5 was prepared by first mixing 2.90 g of solid pyrophosphoric acid ($H_4P_2O_7$; 14.85 mmol, ≥90%; Sigma-Aldrich Chemie GmbH, Taufkirchen, Germany; catalog #83210) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 10 g (62.4 mmol) of synthesized pure EAPA were fed into the glass reactor at a constant feeding rate of 0.33 mL/min by means of a funnel. The EAPA was slowly dropped into the glass reactor and the reaction products were semi-batchwise removed. The liquid products were condensed and collected in an ice-cooled flask, and the gaseous by-products were routed to the off-gas. After an overall process time of 150 min, 0.5 g of mesitylene ($C_6H_3(CH_3)_3$; 4.08 mmol, 98%; Sigma-Aldrich Chemie GmbH, Taufkirchen, Germany; catalog # M7200) were added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 2.8 mol %.

Example 39—Acrylic Acid Synthesis from 2-TFPA with [PBu$_4$]Br and H$_4$P$_2$O$_7$ Molten Salt Catalyst, Molar Ratio of Lactic Acid Equivalent (LAe) to [PBu$_4$]Br to H$_4$P$_2$O$_7$ Equal to 3.6:3.5:1, Temperature 220° C., and No Strip Gas The molten salt catalyst with a molar ratio of 3.5 was prepared by first mixing 2.90 g of solid pyrophosphoric acid ($H_4P_2O_7$; 14.85 mmol, ≥90%; Sigma-Aldrich Chemie GmbH, Taufkirchen, Germany; catalog #83210) and 18 g of solid tetrabutylphosphonium bromide ([PBu$_4$]Br; 51.99 mmol, 98%; Sigma-Aldrich Chemie GmbH, Taufkirchen, Germany; catalog #189138) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 10 g (53.8 mmol) of synthesized pure 2-TFPA were fed into the glass reactor at a constant feeding rate of 0.33 mL/min by means of a funnel. The 2-TFPA was slowly dropped into the glass reactor and the reaction products were semi-batchwise removed. The liquid products were condensed and collected in an ice-cooled flask, and the gaseous by-products were routed to the off-gas. After an overall process time of 150 min, 0.5 g of mesitylene ($C_6H_3(CH_3)_3$; 4.08 mmol, 98%; Sigma-Aldrich Chemie GmbH, Taufkirchen, Germany; catalog # M7200) were added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 5 mol %.

Example 40—Acrylic Acid Synthesis from 2-APA with [pTolPPh$_3$]Br and HBr Molten Salt Catalyst, Molar Ratio of Lactic Acid Equivalent (LAe) to [pTolPPh$_3$]Br to HBr Equal to 9.3:4:1, Temperature 220° C., and No Strip Gas The molten salt catalyst with a molar ratio of 4 was prepared by first mixing 2.43 g of liquid hydrobromic acid (HBr; 14.42 mmol, 48%; Sigma-Aldrich Chemie GmbH, Taufkirchen, Germany; catalog #244260) and 25 g of solid (p-tolyl)triphenylphosphonium bromide ([pTolPPh$_3$]Br; 57.69 mmol, 100%) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a hose pump. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 0.1 g of 3-(Trimethylsilyl)-1-propanesulfonic acid sodium salt (0.44 mmol, 97%; Sigma-Aldrich Chemie GmbH, Taufkirchen, Germany; catalog #178837) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 7.8 mol % and a 2-APA conversion of ≥97 mol %.

Example 41—Acrylic Acid Synthesis from 2-APA with [EtPPh$_3$]Br and HBr Molten Salt Catalyst, Molar Ratio of Lactic Acid Equivalent (LAe) to [EtPPh$_3$]Br to HBr Equal to 10:4:1, Temperature 220° C., and No Strip Gas The molten salt catalyst with a molar ratio of 4 was prepared by first mixing 2.25 g of liquid hydrobromic acid (HBr; 13.35 mmol, 48%; Sigma-Aldrich Chemie GmbH, Taufkirchen, Germany; catalog #244260) and 20 g of solid ethyltriphenylphosphonium bromide ([EtPPh$_3$]Br; 53.33 mmol, 99%; Sigma-Aldrich Chemie GmbH, Taufkirchen, Germany; catalog # E50604) at room temperature and atmospheric conditions in a 100 mL three-necked glass reactor, and then heating the catalyst at a temperature of 220° C. under continuous stirring with an overhead stirrer at a speed of 300 rpm. After the molten salt catalyst reached a constant temperature of 220° C., 17.64 g (133.5 mmol) of synthesized pure 2-APA were fed into the glass reactor at a constant feeding rate of 0.5 mL/min by means of a hose pump. The 2-APA was slowly dropped into the glass reactor and the reaction products were semi-batchwise removed. The liquid products were condensed and collected in an ice-cooled flask, and the gaseous by-products were routed to the off-gas. After an overall process time of 150 min, 0.1 g of 3-(Trimethylsilyl)-1-propanesulfonic acid sodium salt (0.44 mmol, 97%; Sigma-Aldrich Chemie GmbH, Taufkirchen, Germany; catalog #178837) was added to the distillation flask as internal standard and the collected distillate, as well as the molten salt catalyst, were both analyzed via off-line $^1$H NMR (JEOL ECX 400 MHz). $^1$H qNMR analysis of the distillate gave an acrylic acid yield of about 25 mol % and a 2-APA conversion of ≥97 mol %.

Tabulated results from Examples 1 to 41 can be seen in Table 1 below. All reactions were conducted at a constant temperature of the molten salt catalyst of 220° C., except where noted, and with no strip gas, except where noted.

TABLE 1

| Example # | Feed Material | Catalyst—IL | Catalyst—Acid | Molar Ratio of Feed (LAe) to IL to Acid, [-] | Acrylic Acid Yield, [mol %] |
|---|---|---|---|---|---|
| 1 | 2-APA | [PBu$_4$]Br | — | 2.57:1:- | 1.3 |
| 2 | 2-APA | [PBu$_4$]Br | H$_4$P$_2$O$_7$ | 71.8:28:1 | 5.5 |
| 3 | 2-APA | [PBu$_4$]Br | H$_4$P$_2$O$_7$ | 36:14:1 | 7.0 |
| 4 | 2-APA | [PBu$_4$]Br | H$_4$P$_2$O$_7$ | 18:7:1 | 9.6 |

TABLE 1-continued

| Example # | Feed Material | Catalyst—IL | Catalyst—Acid | Molar Ratio of Feed (LAe) to IL to Acid, [-] | Acrylic Acid Yield, [mol %] |
|---|---|---|---|---|---|
| 5 | 2-APA | [PBu$_4$]Br | H$_4$P$_2$O$_7$ | 12.2:4.75:1 | 11.1 |
| 6 | 2-APA | [PBu$_4$]Br | H$_4$P$_2$O$_7$ | 9:3.5:1 | 8.8 |
| 7 | 2-APA | [PBu$_4$]Br | H$_4$P$_2$O$_7$ | 2.57:1:1 | 1.4 |
| 8 | 2-APA | — | H$_4$P$_2$O$_7$ | 1.47:0:1 | 0 |
| 9 | 2-APA | [PBu$_4$]Br | KBr | 12.2:4.75:1 | 0.7 |
| 10 | 2-APA | [PBu$_4$]Br | CaBr$_2$ | 12.2:4.75:1 | 11.8 |
| 11 | 2-APA | [PBu$_4$]Br | MgBr$_2$ | 12.2:4.75:1 | 12.9 |
| 12 | 2-APA | [PBu$_4$]Br | AlBr$_3$ | 12.2:4.75:1 | 14.3 |
| 13 | 2-APA | [PBu$_4$]Br | InBr$_3$ | 12.2:4.75:1 | 0.8 |
| 14 | 2-APA | [PBu$_4$]Br | NiBr$_2$ | 12.2:4.75:1 | 0.5 |
| 15 | 2-APA | [PBu$_4$]Br | CoBr$_2$ | 12.2:4.75:1 | 0.6 |
| 16 | 2-APA | [PBu$_4$]Br | ZnBr$_2$ | 12.2:4.75:1 | 0.7 |
| 17 | 2-APA | [PBu$_4$]Br | FeBr$_3$ | 12.2:4.75:1 | 1.0 |
| 18 | 2-APA | [PBu$_4$]Br | GaBr$_3$ | 14.95:4.75:1 | 1.2 |
| 19 | 2-APA | [PBu$_4$]Br | CuBr$_2$ | 12.2:4.75:1 | 8.2 |
| 20 | 2-APA | [PBu$_4$]Br | HBr/AlBr$_3$ | 12.2:4.75:1 | 9.9 |
| 21 | 2-APA | [PBu$_4$]Br | CH$_3$CO$_2$H | 12.2:4.75:1 | 3.4 |
| 22 | 2-APA | [PBu$_4$]Br | H$_3$PO$_4$ | 12.2:4.75:1 | 6.2 |
| 23 | 2-APA | [PBu$_4$]Br | H$_2$SO$_4$ | 12.2:4.75:1 | 11.8 |
| 24 | 2-APA | [PBu$_4$]Br | HBr | 51.4:20:1 | 7.3 |
| 25 | 2-APA | [PBu$_4$]Br | HBr | 25.7:10:1 | 13 |
| 26 | 2-APA | [PBu$_4$]Br | HBr | 15.7:6:1 | 14.3 |
| 27a | 2-APA | [PBu$_4$]Br | HBr | 12.2:4.75:1 | 18.4 |
| 27b* | 2-APA | [PBu$_4$]Br | HBr | 12.2:4.75:1 | 1 |
| 27c** | 2-APA | [PBu$_4$]Br | HBr | 12.2:4.75:1 | 1 |
| 28 | 2-APA | [PBu$_4$]Br | HBr | 10.3:4:1 | 18.5 |
| 29 | 2-APA | [PBu$_4$]Br | HBr | 5.1:2:1 | 18.7 |
| 30 | 2-APA | — | HBr | 10.3:0:1 | 0 |
| 31^ | 2-APA | [PBu$_4$]Br | H$_4$P$_2$O$_7$ | 24.2:4.75:1 | 32 |
| 32^ | 2-APA | [PBu$_4$]Br | H$_4$P$_2$O$_7$ | 17.7:3.5:1 | 23 |
| 33 | 2-APA | [PBu$_4$]Cl | H$_4$P$_2$O$_7$ | 10.8:4.75:1 | <1 |
| 34 | 2-APA | [PBu$_4$]I | H$_4$P$_2$O$_7$ | 13.9:4.75:1 | <1 |
| 35 | 88 wt % LA | [PBu$_4$]Br | H$_4$P$_2$O$_7$ | 6.6:3.5:1 | 4 |
| 36 | Lactide | [PBu$_4$]Br | H$_4$P$_2$O$_7$ | 9:3.5:1 | 8.8 |
| 37 | ETFP | [PBu$_4$]Br | H$_4$P$_2$O$_7$ | 3.1:3.5:1 | 15.6 |
| 38 | EAPA | [PBu$_4$]Br | H$_4$P$_2$O7 | 4.2:3.5:1 | 2.8 |
| 39 | 2-TFPA | [PBu$_4$]Br | H$_4$P$_2$O$_7$ | 3.6:3.5:1 | 5 |
| 40 | 2-APA | [pTolPPh$_3$]Br | HBr | 9.3:4:1 | 7.8 |
| 41 | 2-APA | [EtPPh$_3$]Br | HBr | 10:4:1 | 25 |

*Conducted at a constant temperature of the molten salt catalyst of 160° C.
**Conducted at a constant temperature of the molten salt catalyst of 180° C.
^Ar strip gas Example 42—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 1:1:0.1, Temperature 150° C., and Reaction Time 48 h 17.31 g of solid tetrabutylphosphonium bromide ([PBu$_4$]Br; 50 mmol, 98%; Sigma-Aldrich Chemie GmbH, Taufkirchen, Germany; catalog #189138) and 3.60 g of solid lactide (25 mmol, L,L lactide, polymer grade, Corbion Purac Co., Lenexa, Kans.) were mixed at room temperature and atmospheric conditions in a 100 mL three-necked glass reactor. 0.77 g of liquid 2-bromopropionic acid (2-BrPA; 5 mmol, 99%; Sigma-Aldrich Chemie GmbH, Taufkirchen, Germany; catalog #B78300) was added to the reaction mixture, thus generating a molar ratio of [PBu$_4$]Br and 2-BrPA of 10. Then, the reaction mixture was heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After an overall process time of 48 h, the hot molten salt is allowed to cool down to room temperature and analyzed via off-line $^1$H NMR (JEOL ECX 400 MHz). $^1$H qNMR analysis of the reaction mixture gave an acrylic acid yield of about 47 mol %.

Example 43—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 1:2:0.1, Temperature 110° C., and Reaction Time 168 h 34.62 g of solid tetrabutylphosphonium bromide ([PBu$_4$]Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 110° C. under continuous stirring with an overhead stirrer at a speed of 300 rpm. After the reaction mixture reached a constant temperature of 110° C., the system was batchwise refluxed and gaseous by-products were routed to the off-gas or collected in a hydrostatic column. After a reaction time of 168 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 24 mol %.

Example 44—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 1:2:0.1, Temperature 130° C., and Reaction Time 168 h 34.62 g of solid tetrabutylphosphonium bromide ([PBu$_4$]Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 130° C. under continuous stirring with an overhead stirrer at a speed of 300 rpm. After the reaction mixture reached a constant temperature of 130° C., the system was batchwise refluxed and gaseous by-products were routed to the off-gas or collected in a hydrostatic column. After a reaction time of 168 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 44 mol %.

Example 45—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 1:2:0.1, Temperature 150° C., and Reaction Time 48 h 34.62 g of solid tetrabutylphosphonium bromide ([PBu$_4$]Br; 100 mmol, 98%; Sigma-Aldrich Chemie GmbH, Taufkirchen, Germany; catalog #189138) and 3.60 g of solid lactide (25 mmol, L,L lactide, polymer grade, Corbion Purac Co., Lenexa, Kans.) were mixed at room temperature and atmospheric conditions in a 100 mL three-necked glass reactor. 0.77 g of liquid 2-bromopropionic acid (2-BrPA; 5 mmol, 99%; Sigma-Aldrich Chemie GmbH, Taufkirchen, Germany; catalog #B78300) was added to the reaction mixture, thus generating a molar ratio of [PBu$_4$]Br and 2-BrPA of 20. Then, the reaction mixture was heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After an overall process time of 48 h, the hot molten salt is allowed to cool down to room temperature and analyzed via off-line $^1$H NMR (JEOL ECX 400 MHz). $^1$H qNMR analysis of the reaction mixture gave an acrylic acid yield of about 52 mol %.

Example 46—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 1:2:0.1, Temperature 150° C., and Reaction Time 96 h 34.62 g of solid tetrabutylphosphonium bromide ([PBu$_4$] Br; 100 mmol, 98%; Sigma-Aldrich Chemie GmbH, Taufkirchen, Germany; catalog #189138) and 5.12 g of liquid lactic acid (50 mmol, 88%; Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 96 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 31 mol %.

Example 47—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 1:2:0.1, Temperature 150° C., and Reaction Time 168 h 34.62 g of solid tetrabutylphosphonium bromide ([PBu$_4$] Br; 100 mmol, 98%; Sigma-Aldrich Chemie GmbH, Taufkirchen, Germany; catalog #189138) and 6.03 g of liquid ethyl lactate (50 mmol, 99%; Sigma-Aldrich Chemie GmbH, Taufkirchen, Germany; catalog # W244007) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 168 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 7 mol %.

Example 48—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 1:2:0.1, Temperature 160° C., and Reaction Time 24 h 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 160° C. under continuous stirring with an overhead stirrer at a speed of 300 rpm. After the reaction mixture reached a constant temperature of 160° C., the system was batchwise refluxed and gaseous by-products were routed to the off-gas or collected in a hydrostatic column. After a reaction time of 24 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 58 mol %.

Example 49—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 1:2:0.1, Temperature 170° C., and Reaction Time 7 h 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 170° C. under continuous stirring with an overhead stirrer at a speed of 300 rpm. After the reaction mixture reached a constant temperature of 170° C., the system was batchwise refluxed and gaseous by-products were routed to the off-gas or collected in a hydrostatic column. After a reaction time of 7 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 56 mol %.

Example 50—Acrylic Acid Synthesis from Lactide
with [PBu$_4$]Br and 2-BrPA Molten Salt Catalyst,
Molar Ratio of Lactic Acid Equivalent (LAe) to
[PBu$_4$]Br to 2-BrPA Equal to 1:2:0.1, Temperature
190° C., and Reaction Time 2 h 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 190° C. under continuous stirring with an overhead stirrer at a speed of 300 rpm. After the reaction mixture reached a constant temperature of 190° C., the system was batchwise refluxed and gaseous by-products were routed to the off-gas or collected in a hydrostatic column. After a reaction time of 2 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 54 mol %.

Example 51—Acrylic Acid Synthesis from Lactide
with [PBu$_4$]Br and 2-BrPA Molten Salt Catalyst,
Molar Ratio of Lactic Acid Equivalent (LAe) to
[PBu$_4$]Br to 2-BrPA Equal to 1:2:0.1, Temperature
220° C., and Reaction Time 0.33 h 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 220° C. under continuous stirring with an overhead stirrer at a speed of 300 rpm. After the reaction mixture reached a constant temperature of 220° C., the system was batchwise refluxed and gaseous by-products were routed to the off-gas or collected in a hydrostatic column. After a reaction time of 0.33 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 50 mol %.

Tabulated results from Examples 42 to 51 can be seen in Table 2 below. In all Examples, the molten salt catalyst included [PBu$_4$]Br and 2-BrPA, and lactide was the lactic acid derivative included in the feed stream.

TABLE 2

| Example # | Molar Ratio of LAe to [PBu$_4$]Br to 2-BrPA, [-] | Reaction Temperature, [° C.] | Reaction Time, [h] | Acrylic Acid Yield, [mol %] |
|---|---|---|---|---|
| 42 | 1:1:0.1 | 150 | 48 | 47 |
| 43 | 1:2:0.1 | 110 | 168 | 24 |
| 44 | 1:2:0.1 | 130 | 168 | 44 |
| 45 | 1:2:0.1 | 150 | 48 | 52 |
| 46 | 1:2:0.1 | 150 | 96 | 31 |
| 47 | 1:2:0.1 | 150 | 168 | 7 |
| 48 | 1:2:0.1 | 160 | 24 | 58 |
| 49 | 1:2:0.1 | 170 | 7 | 56 |
| 50 | 1:2:0.1 | 190 | 2 | 54 |
| 51 | 1:2:0.1 | 220 | 0.33 | 50 |

Example 52—Acrylic Acid Synthesis from Lactide
with [PBu$_4$]Br and MgBr$_2$ Molten Salt Catalyst,
Molar Ratio of Lactic Acid Equivalent (LAe) to
[PBu$_4$]Br to MgBr$_2$ Equal to 1:2:0.1, Temperature
150° C., and Reaction Time 48 h 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.94 g of solid MgBr$_2$ (5 mmol, 98%; Sigma-Aldrich Chemie GmbH, Taufkirchen, Germany; catalog #360074) was then added to the reaction mixture, thus generating a molar ratio of lactic acid equivalent (LAe) to [PBu$_4$]Br to MgBr$_2$ equal to 1:2:0.1. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 48 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 56 mol %.

Example 53—Acrylic Acid Synthesis from Lactide
with [PBu$_4$]Br and H$_4$P$_2$O$_7$ Molten Salt Catalyst,
Molar Ratio of Lactic Acid Equivalent (LAe) to
[PBu$_4$]Br to H$_4$P$_2$O$_7$ Equal to 1:2:0.1, Temperature
150° C., and Reaction Time 96.5 h 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.99 g of solid H$_4$P$_2$O$_7$ (5 mmol, 90%; Sigma-Aldrich Chemie GmbH, Taufkirchen, Germany; catalog #83210) was then added to the reaction mixture, thus generating a molar ratio of lactic acid equivalent (LAe) to [PBu$_4$]Br to H$_4$P$_2$O$_7$ equal to 1:2:0.1. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 96.5 h, the hot molten salt was allowed to cool down to room temperature and was analyzed via off-line $^1$H NMR (JEOL ECX 400

MHz). $^1$H qNMR analysis of the reaction mixture gave an acrylic acid yield (AAY) of about 47 mol %.

Example 54—Acrylic Acid Synthesis from Lactide with [PBu$_4$]Br and HBr Molten Salt Catalyst, Molar Ratio of Lactic Acid Equivalent (LAe) to [PBu$_4$]Br to HBr Equal to 1:2:0.1, Temperature 150° C., and Reaction Time 71 h 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.84 g of liquid HBr (5 mmol, 48%; Sigma-Aldrich Chemie GmbH, Taufkirchen, Germany; catalog #244260) was then added to the reaction mixture, thus generating a molar ratio of lactic acid equivalent (LAe) to [PBu$_4$]Br to HBr equal to 1:2:0.1. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 71 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 43 mol %.

Example 55—Acrylic Acid Synthesis from Lactide with [PBu$_4$]Br and Acetic Acid Molten Salt Catalyst, Molar Ratio of Lactic Acid Equivalent (LAe) to [PBu$_4$]Br to Acetic Acid Equal to 1:2:0.1, Temperature 150° C., and Reaction Time 168 h 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.3 g of liquid acetic acid (5 mmol, 100%; VWR International GmbH, Darmstadt, Germany; catalog #20104.334) was then added to the reaction mixture, thus generating a molar ratio of lactic acid equivalent (LAe) to [PBu$_4$]Br to acetic acid equal to 1:2:0.1. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 168 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 30 mol %.

Example 56—Acrylic Acid Synthesis from Lactide with [PBu$_4$]Br and No Further Acid, Molar Ratio of Lactic Acid Equivalent (LAe) to [PBu$_4$]Br Equal to 1:2, Temperature 150° C., and Reaction Time 168 h 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were mixed at room temperature and atmospheric conditions in a 100 mL three-necked glass reactor, thus generating a molar ratio of lactic acid equivalent (LAe) to [PBu$_4$]Br equal to 1:2. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 168 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 32 mol %.

Tabulated results from Examples 52 to 56 can be seen in Table 3 below. In all Examples, lactide was the lactic acid derivative included in the feed stream, and the molar ratio of lactic acid equivalent (LAe) to [PBu$_4$]Br to acid was equal to 1:2:0.1.

TABLE 3

| Example # | Acid in the Molten Salt Catalyst | Reaction Temperature, [° C.] | Reaction Time, [h] | Acrylic Acid Yield, [mol %] |
|---|---|---|---|---|
| 52 | MgBr$_2$ | 150 | 48 | 56 |
| 53 | H$_4$P$_2$O$_7$ | 150 | 96.5 | 47 |
| 54 | HBr | 150 | 71 | 43 |
| 55 | Acetic Acid | 150 | 168 | 30 |
| 56 | None | 150 | 168 | 32 |

Example 57—Acrylic Acid Synthesis from 2-APA with [PBu$_4$]Br and 2-BrPA Molten Salt Catalyst, Molar Ratio of Lactic Acid Equivalent (LAe) to [PBu$_4$]Br to 2-BrPA Equal to 1:2:0.1, Temperature 150° C., and Reaction Time 168 h 34.62 g of solid tetrabutylphosphonium bromide ([PBu$_4$] Br; 100 mmol, 98%; Sigma-Aldrich Chemie GmbH, Taufkirchen, Germany; catalog #189138) and 6.88 g of synthesized pure 2-APA (50 mmol) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 168 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 42 mol %.

Example 58—Acrylic Acid Synthesis from 2-formyloxypropionic Acid (2-FPA) with [PBu$_4$]Br and 2-BrPA Molten Salt Catalyst, Molar Ratio of Lactic Acid Equivalent (LAe) to [PBu$_4$]Br to 2-BrPA Equal to 1:2.5:0.125, Temperature 150° C., and Reaction Time 72 h 34.62 g of solid tetrabutylphosphonium bromide ([PBu$_4$] Br; 100 mmol, 98%; Sigma-Aldrich Chemie GmbH, Taufkirchen, Germany; catalog #189138) and 4.62 g of synthesized pure 2-FPA (40 mmol) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2.5:0.125. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 72 h, the hot molten salt was allowed to cool down to room temperature and was analyzed via off-line $^1$H NMR (JEOL ECX 400 MHz). $^1$H qNMR analysis of the reaction mixture gave an acrylic acid yield (AAY) of about 35 mol %.

Example 59—2-BrPA Synthesis from Lactide with [MIMBS]Br Molten Salt Catalyst

The molten salt bromination medium was prepared by first mixing 16.370 g of solid MIMBS (75 mmol, *J. Mater. Chem.*, 2001, 11, 1057-1062), 12.642 g of 48 wt % hydrobromic acid (HBr; 75 mmol, 48%; Sigma-Aldrich Chemie GmbH, Taufkirchen, Germany; catalog #244260) and 64 g of cyclohexane (C$_6$H$_{12}$, 0.76 mol, >99.5%, Sigma-Aldrich Chemie GmbH, Taufkirchen, Germany; catalog #33117) at room temperature and atmospheric conditions in a 100 mL three-necked glass reactor. The biphasic reaction mixture was heated to a temperature of 69.8° C. under continuous stirring with a magnetic stirring bar at a speed of 600 rpm. The protic and HBr loaded ionic liquid [MIMBS]Br was received by removing the water using a Dean-Stark-apparatus with external heating to 90° C. and finally decanting the cyclohexane phase after the glass reactor was cooled down to room temperature. After reaction the desired acid amount (75 mmol) was readjusted by adding 3.4 g of 48 wt % hydrobromic acid (HBr; 20 mmol, 48%; Sigma-Aldrich Chemie GmbH, Taufkirchen, Germany; catalog #244260). 1.8 g of solid lactide (12.5 mmol, L,L lactide, polymer grade, Corbion Purac Co., Lenexa, Kans.) were added to the reactor and the activated reaction mixture was heated to 120° C. under continuous stirring with an overhead stirrer at a speed of 600 rpm. The reaction mixture was batchwise refluxed and gaseous by-products were routed to the off-gas or collected in a hydrostatic column. After an overall process time of 300 min, the reaction mixture was quenched with 7.92 g of methanol (CH$_3$OH, 0.25 mol, 99.8%, anhydrous, Sigma-Aldrich Chemie GmbH, Taufkirchen, Germany; catalog #322415) and the reaction mixture was analysed via off-line $^1$H NMR (JEOL ECX 400 MHz). $^1$H qNMR analysis of the reaction mixture gave a 2-BrPA yield of about 60 mol % and selectivity of more than about 95 mol %.

Example 60—Acrylic Acid Synthesis from 2-BrPA with [PBu$_4$]Br Molten Salt Catalyst 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 2.29 g of liquid 2-bromopropionic acid (2-BrPA; 14.83 mmol, 99%; Sigma-Aldrich Chemie GmbH, Taufkirchen, Germany; catalog # B78300) in a 100 mL three-necked glass reactor in a molar ratio of 9:1 at room temperature and atmospheric conditions. The reaction mixture was heated to 160° C. under continuous stirring with a magnetic stirring bar at a speed of 450 rpm. The reaction mixture was batchwise refluxed and gaseous by-products were routed to the off-gas or collected in a hydrostatic column. After an overall process time of 3 h, the hot reaction mixture was allowed to cool down to room temperature and was analysed via off-line $^1$H NMR (JEOL ECX 400 MHz). $^1$H qNMR analysis of the reaction mixture gave an acrylic acid (AA) yield of about 47 mol % and selectivity of more than about 81 mol %.

Example 61—3-BrPA Synthesis from 2-BrPA with [PBu$_4$]Br Molten Salt Catalyst 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 20.68 g of liquid 2-bromopropionic acid (2-BrPA; 133.5 mmol, 99%; Sigma-Aldrich Chemie GmbH, Taufkirchen, Germany; catalog # B78300) in a 100 mL three-necked glass reactor in a molar ratio of 1:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After an overall process time of 20 h, the hot reaction mixture was allowed to cool down to room temperature and was analysed via off-line $^1$H NMR (JEOL ECX 400 MHz). $^1$H qNMR analysis of the isomerization mixture gave a 3-bromopropionic acid (3-BrPA) yield of about 79 mol % and selectivity of more than about 90 mol %.

Example 62—Acrylic Acid Synthesis from 3-BrPA with Trioctylamine (TOA)

285 g of trioctylamine ([CH$_3$(CH$_2$)$_7$]$_3$N; 0.8 mol, 98%; Sigma-Aldrich Chemie GmbH, Taufkirchen, Germany; catalog # T81000) were mixed with 123.4 g of solid 3-bromopropionic acid (3-BrPA; 0.8 mol, 97%; Sigma-Aldrich Chemie GmbH, Taufkirchen, Germany; catalog #101281) in a three-necked glass reactor in a molar ratio of 1:1 at room temperature and atmospheric conditions. The reaction mixture was heated to 180° C. under continuous stirring with a magnetic stirring bar at a speed of 500 rpm. After the reaction mixture reached a constant temperature of 180° C., the reaction products were semi-batchwise removed under reduced pressure (90-100 mbar). The liquid products were condensed and collected in an ice-cooled flask, and the gaseous by-products were routed to the off-gas. After an overall process time of 30 min the collected distillate was analysed via off-line $^1$H NMR (JEOL ECX 400 MHz). $^1$H qNMR analysis of the product mixture gave an acrylic acid yield of about 90 mol % and selectivity of more than about 90 mol %.

Example 63—Acrylic Acid Synthesis from Lactide with [PBu$_4$]Br and 2-BrPA Molten Salt Catalyst, and Molar Ratio of Lactic Acid Equivalent (LAe) to [PBu$_4$]Br to 2-BrPA Equal to 1:2:0.1, Using In-Situ Product Removal Via Reactive Distillation at 100 mbar for 3 Hours 34.62 g of solid tetrabutylphosphonium bromide ([PBu$_4$]Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 190° C. under continuous stirring with a magnetic stirrer at a speed of 800 to 1200 rpm. After the reaction mixture reached a constant temperature of 190° C., a pressure of 100 mbar was applied to start the reactive distillation. The products were collected in cooling trap(s) at temperatures between 0 to −197° C. After 3 hours of reactive distillation the reaction was stopped. Under the chosen reaction conditions polymerization of the highly pure acrylic acid took place in the experimental setup. Therefore no yield was determined.

Example 64—Acrylic Acid Synthesis from Lactide with [PBu$_4$]Br and 2-BrPA Molten Salt Catalyst, and Molar Ratio of Lactic Acid Equivalent (LAe) to [PBu$_4$]Br to 2-BrPA Equal to 1:2:0.1, Using In-Situ Product Removal Via Reactive Distillation at 50 mbar for 3 Hours 34.62 g of solid tetrabutylphosphonium bromide ([PBu$_4$]Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 190° C. under continuous stirring with a magnetic stirrer at a speed of 800 to 1200 rpm. After the reaction mixture reached a constant temperature of 190° C., a pressure of 50 mbar was applied to start the reactive distillation. The products were collected in cooling trap(s) at temperatures between 0 to −197° C. After 3 hours of reactive distillation the reaction was stopped. Under the chosen reaction conditions polymerization of the highly pure acrylic acid took place in the experimental setup.

Example 65—Acrylic Acid Synthesis from Lactide with [PBu$_4$]Br and 2-BrPA Molten Salt Catalyst, and Molar Ratio of Lactic Acid Equivalent (LAe) to [PBu$_4$]Br to 2-BrPA Equal to 1:2:0.1, Using In-Situ Product Removal Via Reactive Distillation at 20 mbar for 3 Hours 34.62 g of solid tetrabutylphosphonium bromide ([PBu$_4$]Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 190° C. under continuous stirring with a magnetic stirrer at a speed of 800 to 1200 rpm. After the reaction mixture reached a constant temperature of 190° C., a pressure of 20 mbar was applied to start the reactive distillation. The products were collected in cooling trap(s) at temperatures between 0 to −197° C. By-products were routed to the off-gas. Under the chosen reaction conditions polymerization of the highly pure acrylic acid took place in the experimental setup. Therefore no yield was determined.

Example 66a—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 1:2:0.1, Water Content of about 0.3 wt %, and Using In-Situ Product Removal Via Reactive Distillation at 10 mbar for 3 Hours 34.62 g of solid tetrabutylphosphonium bromide ([PBu$_4$]Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The water content, as measured by Karl Fischer titration, was about 0.3 wt %. The reaction mixture was then heated to a reaction temperature of 190° C. under continuous stirring with a magnetic stirrer at a speed of 800 to 1200 rpm. After the reaction mixture reached a constant temperature of 190° C., a pressure of 10 mbar was applied to start the reactive distillation. The products were collected in cooling trap(s) at temperatures between 0 to −197° C. After 3 hours of reactive distillation, the hot molten salt and the distillate were analyzed via off-line $^1$H NMR (JEOL ECX 400 MHz). $^1$H qNMR analysis of the reaction mixture gave an acrylic acid yield of about 11 mol %, $^1$H qNMR analysis of the distillate gave an acrylic acid yield of about 69 mol %, giving an overall acrylic acid yield in this reactive distillation of about 80 mol %.

Example 66b—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 1:2:0.1, Water Content of about 1.5 wt %, and Using In-Situ Product Removal Via Reactive Distillation at 10 mbar for 3 Hours 34.62 g of solid tetrabutylphosphonium bromide ([PBu$_4$]Br; 100 mmol, 98%; Sigma-Aldrich Chemie GmbH, Taufkirchen, Germany; catalog #189138) and 3.62 g of solid lactide (25.1 mmol, L,L lactide, polymer grade, Corbion Purac Co., Lenexa, Kans.) were first mixed at room temperature and atmospheric conditions in a 100 mL three-necked glass reactor. 0.777 g of liquid 2-BrPA (5.03 mmol, 99%; Sigma-Aldrich Chemie GmbH, Taufkirchen, Germany; catalog # B78300) and 0.585 g distilled water were then added to the reaction mixture, thus generating a molar ratio of lactic acid equivalent (LAe) to [PBu$_4$]Br to 2-BrPA equal to 1:2:0.1, and water content of about 1.5%. The reaction mixture was then heated to a reaction temperature of 190° C. under continuous stirring with a magnetic stirrer at a speed of 800 rpm. After the reaction mixture reached a constant temperature of 190° C., a pressure of 10 mbar was applied to start the reactive distillation. By-products were routed to the off-gas. After 3 hours of reactive distillation, the hot molten salt and the distillate were analyzed via off-line $^1$H NMR (JEOL ECX 400 MHz). $^1$H qNMR analysis of the hot molten salt gave an acrylic acid yield of about 11 mol %, and $^1$H qNMR analysis of the distillate gave an acrylic acid yield of about 62 mol %. Thus, the overall acrylic acid yield in this reactive distillation was about 73 mol %.

Example 66c—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 1:2:0.1, Water Content of about 3.6 wt %, and Using In-Situ Product Removal Via Reactive Distillation at 10 mbar for 3 Hours 34.62 g of solid tetrabutylphosphonium bromide ([PBu$_4$] Br; 100 mmol, 98%; Sigma-Aldrich Chemie GmbH, Taufkirchen, Germany; catalog #189138) and 3.60 g of solid lactide (25 mmol, L,L lactide, polymer grade, Corbion Purac Co., Lenexa, Kans.) were first mixed at room temperature and atmospheric conditions in a 100 mL three-necked glass reactor. 0.781 g of liquid 2-BrPA (5.05 mmol, 99%; Sigma-Aldrich Chemie GmbH, Taufkirchen, Germany; catalog # B78300) and 1.442 g distilled water were then added to the reaction mixture, thus generating a molar ratio of lactic acid equivalent (LAe) to [PBu$_4$]Br to 2-BrPA equal to 1:2:0.1, and water content of about 3.6 wt %. The reaction mixture was then heated to a reaction temperature of 190° C. under continuous stirring with a magnetic stirrer at a speed of 800 rpm. After the reaction mixture reached a constant temperature of 190° C., a pressure of 10 mbar was applied to start the reactive distillation. By-products were routed to the off-gas. After 3 hours of reactive distillation, the hot molten salt and the distillate were analyzed via off-line $^1$H NMR (JEOL ECX 400 MHz). $^1$H qNMR analysis of the hot molten salt gave an acrylic acid yield of about 12 mol %, and $^1$H qNMR analysis of the distillate gave an acrylic acid yield of about 65 mol %. Thus, the overall acrylic acid yield in this reactive distillation was about 77 mol %.

Tabulated results from Examples 66a, 66b, and 66c can be seen in Table 4 below. In all Examples, lactide was the lactic acid derivative included in the feed stream, and the molar ratio of lactic acid equivalent (LAe) to [PBu$_4$]Br to 2-BrPA was equal to 1:1:0.1.

TABLE 4

| Example # | Water Content, [wt %] | Reaction Temperature, [° C.] | Reaction Time, [h] | Acrylic Acid Yield, [mol %] |
|---|---|---|---|---|
| 66a | 0.3 | 190 | 3 | 80 |
| 66b | 1.5 | 190 | 3 | 73 |
| 66c | 3.6 | 190 | 3 | 77 |

Example 67—Acrylic Acid Synthesis from Lactide with [PBu$_4$]Br and 2-BrPA Molten Salt Catalyst, and Molar Ratio of Lactic Acid Equivalent (LAe) to [PBu$_4$]Br to 2-BrPA Equal to 1:2:0.1, Using In-Situ Product Removal Via Reactive Distillation at 5 mbar for 3 Hours 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 190° C. under continuous stirring with a magnetic stirrer at a speed of 800 to 1200 rpm. After the reaction mixture reached a constant temperature of 190° C., a pressure of 5 mbar was applied to start the reactive distillation. The products were collected in cooling trap(s) at temperatures between 0 to −197° C. After 3 hours of reactive distillation, the hot molten salt and the distillate were analyzed via off-line $^1$H NMR (JEOL ECX 400 MHz). $^1$H qNMR analysis of the reaction mixture gave an acrylic acid yield of about 8 mol %, $^1$H qNMR analysis of the distillate gave an acrylic acid yield of about 62 mol %, giving an overall acrylic acid yield in this reactive distillation of about 70 mol %.

Example 68—Acrylic Acid Synthesis from Lactide with [PBu$_4$]Br and 2-BrPA Molten Salt Catalyst, and Molar Ratio of Lactic Acid Equivalent (LAe) to [PBu$_4$]Br to 2-BrPA Equal to 1:2:0.1, Using In-Situ Product Removal Via Reactive Distillation at 10 mbar for 1 Hour 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 190° C. under continuous stirring with a magnetic stirrer at a speed of 800 to 1200 rpm. After the reaction mixture reached a constant temperature of 190° C., a pressure of 10 mbar was applied to start the reactive distillation. The products were collected in cooling trap(s) at temperatures between 0 to −197° C. After 1 hour of reactive distillation, the hot molten salt and the distillate were analyzed via off-line $^1$H NMR (JEOL ECX 400 MHz). $^1$H qNMR analysis of the reaction mixture gave an acrylic acid yield of about 24 mol %, $^1$H qNMR analysis of the distillate gave an acrylic acid yield of about 29 mol %, giving an overall acrylic acid yield in this reactive distillation of about 53 mol %.

Example 69—Acrylic Acid Synthesis from Lactide with [PBu$_4$]Br and 2-BrPA Molten Salt Catalyst, and Molar Ratio of Lactic Acid Equivalent (LAe) to [PBu$_4$]Br to 2-BrPA Equal to 1:2:0.1, Using In-Situ Product Removal Via Reactive Distillation at 10 mbar for 2 Hours 34.62 g of solid tetrabutylphosphonium bromide ([PBu$_4$] Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 190° C. under continuous stirring with a magnetic stirrer at a speed of 800 to 1200 rpm. After the reaction mixture reached a constant temperature of 190° C., a pressure of 10 mbar was applied to start the reactive distillation. The products were collected in cooling trap(s) at temperatures between 0 to −197° C. After 2 hours of reactive distillation, the hot molten salt and the distillate were analyzed via off-line $^1$H NMR (JEOL ECX 400 MHz). $^1$H qNMR analysis of the reaction mixture gave an acrylic acid yield of about 20 mol %, $^1$H qNMR analysis of the distillate gave an acrylic acid yield of about 42 mol %, giving an overall acrylic acid yield in this reactive distillation of about 62 mol %.

Example 70—Acrylic Acid Synthesis from Lactide with [PBu$_4$]Br and 2-BrPA Molten Salt Catalyst, and Molar Ratio of Lactic Acid Equivalent (LAe) to [PBu$_4$]Br to 2-BrPA Equal to 1:2:0.1, Using In-Situ Product Removal Via Reactive Distillation at 10 mbar for 4 Hours 34.62 g of solid tetrabutylphosphonium bromide ([PBu$_4$]Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 1:2:0.1. The reaction mixture was then heated to a reaction temperature of 190° C. under continuous stirring with a magnetic stirrer at a speed of 800 to 1200 rpm. After the reaction mixture reached a constant temperature of 190° C., a pressure of 10 mbar was applied to start the reactive distillation. The products were collected in cooling trap(s) at temperatures between 0 to −197° C. After 4 hours of reactive distillation, the hot molten salt and the distillate were analyzed via off-line $^1$H NMR (JEOL ECX 400 MHz). $^1$H qNMR analysis of the reaction mixture gave an acrylic acid yield of about 3 mol %, $^1$H qNMR analysis of the distillate gave an acrylic acid yield of about 72 mol %, giving an overall acrylic acid yield in this reactive distillation of about 75 mol %.

Procedure 1—Stability of Solid Material Samples in Liquid Chemicals

This procedure describes the treatment of solid material samples in liquid chemicals at certain temperatures and the related analysis. The solid material sample with a size of 15 mm×15 mm×2 mm is cleaned and analyzed by weighing, optical microscopy and scanning electron microscopy in advance to the treatment. The treatment is performed in a borosilicate glass 3.3 vessel with 30 mm diameter and 200 mm height. 30 ml liquid chemical is fed into the vessel covering the sample entirely. The chemical is stirred by a borosilicate glass 3.3 coated magnetic stir bar during the treatment to minimalize temperature and concentration gradients. The sample is held in place by a support 15 mm above the vessel bottom to avoid mechanical contact with the stir bar. The vessel is open to atmosphere at the top through a vertical 1 meter long and 10 mm diameter fluorinated ethylene propylene tube acting as a reflux condenser at room temperature. The bottom half of the vessel is including the sample and the chemical is heated to a certain temperature "T" for a certain time "t"—individual for each treatment. After the treatment, the sample is again cleaned and analyzed by weighing, optical microscopy and scanning electron microscopy.

Example 71—Stability of Borosilicate Glass 3.3 (Boro 3.3) Versus 2-Acetoxypropionic Acid (2-APA)

According to PROCEDURE 1, Boro 3.3 was tested for stability versus 2-APA at T=150° C. for t=24 h. The mass change was less than 0.1% and no color change, no surface topology change and no haptic change could be observed. Boro 3.3 is stated as stable versus 2-APA up to at least 150° C.

Example 72—Stability of Quartz Glass (SiO$_2$) Versus 2-Acetoxypropionic Acid (2-APA)

According to PROCEDURE 1, SiO$_2$ was tested for stability versus 2-APA at T=150° C. for t=24 h. The mass change was less than 0.1% and no color change, no surface topology change and no haptic change could be observed. SiO$_2$ is stated as stable versus 2-APA up to at least 150° C.

Example 73—Stability of Hastelloy C-276 (C-276) Versus 2-Acetoxypropionic Acid (2-APA)

According to PROCEDURE 1, C-276 was tested for stability versus 2-APA at T=150° C. for t=24 h. The mass change was less than 0.1% and no color change, no surface topology change and no haptic change could be observed. C-276 is stated as stable versus 2-APA up to at least 150° C.

Example 74—Stability of Stainless Steel 1.4571 (1.4571) Versus 2-Acetoxypropionic Acid (2-APA)

According to PROCEDURE 1, 1.4571 was tested for stability versus 2-APA at T=150° C. for t=24 h. The mass change was less than 0.1% and no color change, no surface topology change and no haptic change could be observed. 1.4571 is stated as stable versus 2-APA up to at least 150° C.

Example 75—Stability of Carbon Steel S235 (S235) Versus 2-Acetoxypropionic Acid (2-APA)

According to PROCEDURE 1, S235 was tested for stability versus 2-APA at T=150° C. for t=24 h. Corrosion could be observed on the surface. S235 is stated as not stable versus 2-APA at 150° C.

Example 76—Stability of Aluminum (Al) Versus 2-Acetoxypropionic Acid (2-APA)

According to PROCEDURE 1, Al was tested for stability versus 2-APA at T=150° C. for t=24 h. The mass change was less than 0.1% and no color change and no haptic change could be observed. The surface was slightly roughened. Al is stated as stable with minor changes versus 2-APA up to at least 150° C.

Example 77—Stability of Polytetrafluorethylene (PTFE) Versus 2-Acetoxypropionic Acid (2-APA)

According to PROCEDURE 1, PTFE was tested for stability versus 2-APA at T=150° C. for t=24 h. The mass change was less than 0.1% and no color change, no surface topology change and no haptic change could be observed. PTFE is stated as stable versus 2-APA up to at least 150° C.

Example 78—Stability of Fluorinated Ethylene Propylene (FEP) Versus 2-Acetoxypropionic Acid (2-APA)

According to PROCEDURE 1, FEP was tested for stability versus 2-APA at T=150° C. for t=24 h. The mass change was less than 0.1% and no color change, no surface topology change and no haptic change could be observed. FEP is stated as stable versus 2-APA up to at least 150° C.

Example 79—Stability of Perfluoroalkoxy Alkane (PFA) Versus 2-Acetoxypropionic Acid (2-APA)

According to PROCEDURE 1, PFA was tested for stability versus 2-APA at T=150° C. for t=24 h. The mass change was less than 0.1% and no color change, no surface topology change and no haptic change could be observed. PFA is stated as stable versus 2-APA up to at least 150° C.

Example 80—Stability of Polyether Ether Ketone (PEEK) Versus 2-Acetoxypropionic Acid (2-APA)

According to PROCEDURE 1, PEEK was tested for stability versus 2-APA at T=150° C. for t=24 h. The mass change was less than 0.1% and no surface topology change and no haptic change could be observed. The sample showed a slight change of its color. PEEK is stated as stable with minor changes versus 2-APA up to at least 150° C.

Example 81—Stability of Fluoroelastomer (FKM) Versus 2-Acetoxypropionic Acid (2-APA)

According to PROCEDURE 1, FKM was tested for stability versus 2-APA at T=150° C. for t=24 h. The mass increase was more than 10% and the sample cracked. The chemical showed color changes. FKM is stated as not stable versus 2-APA at 150° C.

Example 82—Stability of Silicone Rubber (Sil) Versus 2-Acetoxypropionic Acid (2-APA)

According to PROCEDURE 1, Sil was tested for stability versus 2-APA at T=150° C. for t=24 h. The mass increase was less than 10% and reversible after drying and no surface topology change and no haptic change could be observed. Sil is stated as stable with minor changes versus 2-APA up to at least 150° C.

Example 83—Stability of Borosilicate Glass 3.3 (Boro 3.3) Versus 2-Bromopropionic Acid (2-BrPA)

According to PROCEDURE 1, Boro 3.3 was tested for stability versus 2-BrPA at T=100° C. for t=24 h. The mass change was less than 0.1% and no color change, no surface topology change and no haptic change could be observed. Boro 3.3 is stated as stable versus 2-BrPA up to at least 100° C.

Example 84—Stability of Quartz Glass ($SiO_2$) Versus 2-Bromopropionic Acid (2-BrPA)

According to PROCEDURE 1, $SiO_2$ was tested for stability versus 2-BrPA at T=100° C. for t=24 h. The mass change was less than 0.1% and no color change, no surface topology change and no haptic change could be observed. $SiO_2$ is stated as stable versus 2-BrPA up to at least 100° C.

Example 85—Stability of Stainless Steel 1.4571 (1.4571) Versus 2-Bromopropionic Acid (2-BrPA)

According to PROCEDURE 1, 1.4571 was tested for stability versus 2-BrPA at T=100° C. for t=24 h. Corrosion could be observed on the surface. 1.4571 is stated as not stable versus 2-BrPA at 100° C.

Example 86—Stability of Carbon Steel S235 (S235) Versus 2-Bromopropionic Acid (2-BrPA)

According to PROCEDURE 1, S235 was tested for stability versus 2-BrPA at T=100° C. for t=24 h. Corrosion could be observed on the surface. S235 is stated as not stable versus 2-BrPA at 100° C.

Example 87—Stability of Aluminum (Al) Versus 2-Bromopropionic Acid (2-BrPA)

According to PROCEDURE 1, Al was tested for stability versus 2-BrPA at T=100° C. for t=24 h. The mass change was less than 0.1% and no color change, no surface topology change and no haptic change could be observed. Al is stated as stable versus 2-BrPA up to at least 100° C.

Example 88—Stability of Polytetrafluorethylene (PTFE) Versus 2-Bromopropionic Acid (2-BrPA)

According to PROCEDURE 1, PTFE was tested for stability versus 2-BrPA at T=100° C. for t=24 h. The mass change was less than 0.1% and no color change, no surface topology change and no haptic change could be observed. PTFE is stated as stable versus 2-BrPA up to at least 100° C.

Example 89—Stability of Fluorinated Ethylene Propylene (FEP) Versus 2-Bromopropionic Acid (2-BrPA)

According to PROCEDURE 1, FEP was tested for stability versus 2-BrPA at T=100° C. for t=24 h. The mass change was less than 0.1% and no color change, no surface topology change and no haptic change could be observed. FEP is stated as stable versus 2-BrPA up to at least 100° C.

Example 90—Stability of Perfluoroalkoxy Alkane (PFA) Versus 2-Bromopropionic Acid (2-BrPA)

According to PROCEDURE 1, PFA was tested for stability versus 2-BrPA at T=100° C. for t=24 h. The mass change was less than 0.1% and no color change, no surface topology change and no haptic change could be observed. PFA is stated as stable versus 2-BrPA up to at least 100° C.

Example 91—Stability of Polyether Ether Ketone (PEEK) Versus 2-Bromopropionic Acid (2-BrPA)

According to PROCEDURE 1, PEEK was tested for stability versus 2-BrPA at T=100° C. for t=24 h. The mass change was less than 0.1% and no surface topology change and no haptic change could be observed. The sample showed a slight change of its color. PEEK is stated as stable with minor changes versus 2-BrPA up to at least 100° C.

Example 92—Stability of Fluoroelastomer (FKM) Versus 2-Bromopropionic Acid (2-BrPA)

According to PROCEDURE 1, FKM was tested for stability versus 2-BrPA at T=100° C. for t=24 h. The mass increase was more than 10%. The surface was roughened. FKM is stated as not stable versus 2-BrPA at 100° C.

Example 93—Stability of Silicone Rubber (Sil) Versus 2-Bromopropionic Acid (2-BrPA)

According to PROCEDURE 1, Sil was tested for stability versus 2-BrPA at T=100° C. for t=24 h. The mass increase was more than 10%. The color changed. Sil is stated as not stable versus 2-BrPA at 100° C.

Example 94—Stability of Borosilicate Glass 3.3 (Boro 3.3) Versus Acetic Acid 75 Weight Percent Aqueous Solution (AcOH75)

According to PROCEDURE 1, Boro 3.3 was tested for stability versus AcOH75 at T=90° C. for t=24 h. The mass change was less than 0.1% and no color change, no surface topology change and no haptic change could be observed. Boro 3.3 is stated as stable versus AcOH75 up to at least 90° C.

Example 95—Stability of Quartz Glass (SiO$_2$) Versus Acetic Acid 75 Weight Percent Aqueous Solution (AcOH75)

According to PROCEDURE 1, SiO$_2$ was tested for stability versus AcOH75 at T=90° C. for t=24 h. The mass change was less than 0.1% and no color change, no surface topology change and no haptic change could be observed. SiO$_2$ is stated as stable versus AcOH75 up to at least 90° C.

Example 96—Stability of Titanium Grade 2 (TiG2) Versus Acetic Acid 75 Weight Percent Aqueous Solution (AcOH75)

According to PROCEDURE 1, TiG2 was tested for stability versus AcOH75 at T=90° C. for t=24 h. The mass change was less than 0.1% and no color change, no surface topology change and no haptic change could be observed. TiG2 is stated as stable versus AcOH75 up to at least 90° C.

Example 97—Stability of Stainless Steel 1.4571 (1.4571) Versus Acetic Acid 75 Weight Percent Aqueous Solution (AcOH75)

According to PROCEDURE 1, 1.4571 was tested for stability versus AcOH75 at T=90° C. for t=24 h. The mass change was less than 0.1% and no color change, no surface topology change and no haptic change could be observed. 1.4571 is stated as stable versus AcOH75 up to at least 90° C.

Example 98—Stability of Carbon Steel S235 (S235) Versus Acetic Acid 75 Weight Percent Aqueous Solution (AcOH75)

According to PROCEDURE 1, S235 was tested for stability versus AcOH75 at T=90° C. for t=24 h. Corrosion could be observed on the surface. S235 is stated as not stable versus AcOH75 at 90° C.

Example 99—Stability of Aluminum (Al) Versus Acetic Acid 75 Weight Percent Aqueous Solution (AcOH75)

According to PROCEDURE 1, Al was tested for stability versus AcOH75 at T=90° C. for t=24 h. The mass change was less than 0.1%. Color change and the surface were slightly roughened. Al is stated as not stable versus AcOH75 up to at least 90° C.

Example 100—Stability of Polytetrafluorethylene (PTFE) Versus Acetic Acid 75 Weight Percent Aqueous Solution (AcOH75)

According to PROCEDURE 1, PTFE was tested for stability versus AcOH75 at T=90° C. for t=24 h. The mass change was less than 0.1% and no color change, no surface topology change and no haptic change could be observed. PTFE is stated as stable versus AcOH75 up to at least 90° C.

Example 101—Stability of Fluorinated Ethylene Propylene (FEP) Versus Acetic Acid 75 Weight Percent Aqueous Solution (AcOH75)

According to PROCEDURE 1, FEP was tested for stability versus AcOH75 at T=90° C. for t=24 h. The mass change was less than 0.1% and no color change, no surface topology change and no haptic change could be observed. FEP is stated as stable versus AcOH75 up to at least 90° C.

Example 102—Stability of Perfluoroalkoxy Alkane (PFA) Versus Acetic Acid 75 Weight Percent Aqueous Solution (AcOH75)

According to PROCEDURE 1, PFA was tested for stability versus AcOH75 at T=90° C. for t=24 h. The mass change was less than 0.1% and no color change, no surface topology change and no haptic change could be observed. PFA is stated as stable versus AcOH75 up to at least 90° C.

Example 103—Stability of Polyether Ether Ketone (PEEK) Versus Acetic Acid 75 Weight Percent Aqueous Solution (AcOH75)

According to PROCEDURE 1, PEEK was tested for stability versus AcOH75 at T=90° C. for t=24 h. The mass change was less than 0.1% and no color change, no surface topology change and no haptic change could be observed. PEEK is stated as stable versus AcOH75 up to at least 90° C.

Example 104—Stability of Fluoroelastomer (FKM) Versus Acetic Acid 75 Weight Percent Aqueous Solution (AcOH75)

According to PROCEDURE 1, FKM was tested for stability versus AcOH75 at T=90° C. for t=24 h. The mass increase was more than 10% and the sample cracked. The chemical showed color changes. FKM is stated as not stable versus AcOH75 at 90° C.

Example 105—Stability of Silicone Rubber (Sil) Versus Acetic Acid 75 Weight Percent Aqueous Solution (AcOH75)

According to PROCEDURE 1, Sil was tested for stability versus AcOH75 at T=90° C. for t=24 h. The mass increase was less than 10% and reversible after drying and no surface topology change and no haptic change could be observed. Sil is stated as stable with minor changes versus AcOH75 up to at least 90° C.

Example 106—Stability of Borosilicate Glass 3.3 (Boro 3.3) Versus Acrylic Acid (AA)

According to PROCEDURE 1, Boro 3.3 was tested for stability versus AA at T=20° C. for t=24 h. The mass change was less than 0.1% and no color change, no surface topology change and no haptic change could be observed. Boro 3.3 is stated as stable versus AA up to at least 20° C.

Example 107—Stability of Quartz Glass ($SiO_2$) Versus Acrylic Acid (AA)

According to PROCEDURE 1, $SiO_2$ was tested for stability versus AA at T=20° C. for t=24 h. The mass change was less than 0.1% and no color change, no surface topology change and no haptic change could be observed. $SiO_2$ is stated as stable versus AA up to at least 20° C.

Example 108—Stability of Titanium Grade 2 (TiG2) Versus Acrylic Acid (AA)

According to PROCEDURE 1, TiG2 was tested for stability versus AA at T=20° C. for t=24 h. The mass change was less than 0.1% and no color change, no surface topology change and no haptic change could be observed. TiG2 is stated as stable versus AA up to at least 20° C.

Example 109—Stability of Stainless Steel 1.4571 (1.4571) Versus Acrylic Acid (AA)

According to PROCEDURE 1, 1.4571 was tested for stability versus AA at T=20° C. for t=24 h. The mass change was less than 0.1% and no color change, no surface topology change and no haptic change could be observed. 1.4571 is stated as stable versus AA up to at least 20° C.

Example 110—Stability of Carbon Steel S235 (S235) Versus Acrylic Acid (AA)

According to PROCEDURE 1, S235 was tested for stability versus AA at T=20° C. for t=24 h. Corrosion could be observed on the surface. S235 is stated as not stable versus AA at 20° C.

Example 111—Stability of Aluminum (Al) Versus Acrylic Acid (AA)

According to PROCEDURE 1, Al was tested for stability versus AA at T=20° C. for t=24 h. The mass change was less than 0.1% and no color change, no surface topology change and no haptic change could be observed. Al is stated as stable versus AA up to at least 20° C.

Example 112—Stability of Polytetrafluorethylene (PTFE) Versus Acrylic Acid (AA)

According to PROCEDURE 1, PTFE was tested for stability versus AA at T=20° C. for t=24 h. The mass change was less than 0.1% and no color change, no surface topology change and no haptic change could be observed. PTFE is stated as stable versus AA up to at least 20° C.

Example 113—Stability of Fluorinated Ethylene Propylene (FEP) Versus Acrylic Acid (AA)

According to PROCEDURE 1, FEP was tested for stability versus AA at T=20° C. for t=24 h. The mass change was less than 0.1% and no color change, no surface topology change and no haptic change could be observed. FEP is stated as stable versus AA up to at least 20° C.

Example 114—Stability of Perfluoroalkoxy Alkane (PFA) Versus Acrylic Acid (AA)

According to PROCEDURE 1, PFA was tested for stability versus AA at T=20° C. for t=24 h. The mass change was less than 0.1% and no color change, no surface topology change and no haptic change could be observed. PFA is stated as stable versus AA up to at least 20° C.

Example 115—Stability of Polyether Ether Ketone (PEEK) Versus Acrylic Acid (AA)

According to PROCEDURE 1, PEEK was tested for stability versus AA at T=20° C. for t=24 h. The mass change was less than 0.1% and no color change, no surface topology change and no haptic change could be observed. PEEK is stated as stable versus AA up to at least 20° C.

Example 116—Stability of Fluoroelastomer (FKM) Versus Acrylic Acid (AA)

According to PROCEDURE 1, FKM was tested for stability versus AA at T=20° C. for t=24 h. The mass increase was more than 10%. FKM is stated as not stable versus AA at 20° C.

Example 117—Stability of Silicone Rubber (Sil) Versus Acrylic Acid (AA)

According to PROCEDURE 1, Sil was tested for stability versus AA at T=20° C. for t=24 h. The mass increase was more than 10%. The color changed. Sil is stated as not stable versus AA at 20° C.

Example 118—Stability of Borosilicate Glass 3.3 (Boro 3.3) Versus Lactic Acid 88 Weight Percent Aqueous Solution (LA88)

According to PROCEDURE 1, Boro 3.3 was tested for stability versus LA88 at T=150° C. for t=168 h. The mass change was less than 0.1% and no color change, no surface topology change and no haptic change could be observed. Boro 3.3 is stated as stable versus LA88 up to at least 150° C.

Example 119—Stability of Quartz Glass (SiO$_2$) Versus Lactic Acid 88 Weight Percent Aqueous Solution (LA)

According to PROCEDURE 1, SiO$_2$ was tested for stability versus LA88 at T=150° C. for t=168 h. The mass change was less than 0.1% and no color change, no surface topology change and no haptic change could be observed. SiO$_2$ is stated as stable versus LA88 up to at least 150° C.

Example 120—Stability of Titanium Grade 2 (TiG2) Versus Lactic Acid 88 Weight Percent Aqueous Solution (LA)

According to PROCEDURE 1, TiG2 was tested for stability versus LA88 at T=150° C. for t=168 h. The mass change was less than 0.1% and no color change, no surface topology change and no haptic change could be observed. TiG2 is stated as stable versus LA88 up to at least 150° C.

Example 121—Stability of Hastelloy C-276 (C-276) Versus Lactic Acid 88 Weight Percent Aqueous Solution (LA)

According to PROCEDURE 1, C-276 was tested for stability versus LA88 at T=150° C. for t=168 h. Corrosion could be observed on the surface. C-276 is stated as not stable versus LA88 at 150° C.

Example 122—Stability of Carbon Steel S235 (S235) Versus Lactic Acid 88 Weight Percent Aqueous Solution (LA)

According to PROCEDURE 1, S235 was tested for stability versus LA88 at T=150° C. for t=168 h. Corrosion could be observed on the surface. S235 is stated as not stable versus LA88 at 150° C.

Example 123—Stability of Aluminum (Al) Versus Lactic Acid 88 Weight Percent Aqueous Solution (LA)

According to PROCEDURE 1, Al was tested for stability versus LA88 at T=150° C. for t=168 h. The mass change was less than 0.1%. Color change could be observed. The surface was slightly roughened. Al is stated as stable with minor changes versus LA88 up to at least 150° C.

Example 124—Stability of Polytetrafluorethylene (PTFE) Versus Lactic Acid 88 Weight Percent Aqueous Solution (LA)

According to PROCEDURE 1, PTFE was tested for stability versus LA88 at T=150° C. for t=168 h. The mass change was less than 0.1% and no color change, no surface topology change and no haptic change could be observed. PTFE is stated as stable versus LA88 up to at least 150° C.

Example 125—Stability of Fluorinated Ethylene Propylene (FEP) Versus Lactic Acid 88 Weight Percent Aqueous Solution (LA)

According to PROCEDURE 1, FEP was tested for stability versus LA88 at T=150° C. for t=168 h. The mass change was less than 0.1% and no color change, no surface topology change and no haptic change could be observed. FEP is stated as stable versus LA88 up to at least 150° C.

Example 126—Stability of Perfluoroalkoxy Alkane (PFA) Versus Lactic Acid 88 Weight Percent Aqueous Solution (LA)

According to PROCEDURE 1, PFA was tested for stability versus LA88 at T=150° C. for t=168 h. The mass change was less than 0.1% and no color change, no surface topology change and no haptic change could be observed. PFA is stated as stable versus LA88 up to at least 150° C.

Example 127—Stability of Polyether Ether Ketone (PEEK) Versus Lactic Acid 88 Weight Percent Aqueous Solution (LA)

According to PROCEDURE 1, PEEK was tested for stability versus LA88 at T=150° C. for t=168 h. The mass change was less than 0.1% and no color change, no surface topology change and no haptic change could be observed. PEEK is stated as stable versus LA88 up to at least 150° C.

Example 128—Stability of Perfluoroelastomer (FFKM) Versus Lactic Acid 88 Weight Percent Aqueous Solution (LA)

According to PROCEDURE 1, FFKM was tested for stability versus LA88 at T=150° C. for t=168 h. The mass increase was less than 10% and no color change could be observed. FFKM is stated as stable with minor changes versus LA88 up to at least 150° C.

Example 129—Stability of Fluoroelastomere (FKM) Versus Lactic Acid 88 Weight Percent Aqueous Solution (LA)

According to PROCEDURE 1, FKM was tested for stability versus LA88 at T=150° C. for t=168 h. The mass increase was more than 10%. FKM is stated as not stable versus LA88 at 150° C.

Example 130—Stability of Silicone Rubber (Sil) Versus Lactic Acid 88 Weight Percent Aqueous Solution (LA)

According to PROCEDURE 1, Sil was tested for stability versus LA88 at T=250° C. for t=168 h. The mass increase was more than 10%. The color changed. Sil is stated as not stable versus LA88 at 250° C.

Example 131—Stability of Borosilicate Glass 3.3 (Boro 3.3) Versus Tetrabutylphosphonium Bromide ([PBu$_4$]Br)

According to PROCEDURE 1, Boro 3.3 was tested for stability versus [PBu$_4$]Br at T=250° C. for t=168 h. The mass change was less than 0.1% and no color change, no surface topology change and no haptic change could be observed. Boro 3.3 is stated as stable versus [PBu$_4$]Br up to at least 250° C.

Example 132—Stability of Quartz Glass (SiO$_2$) Versus Tetrabutylphosphonium Bromide ([PBu$_4$]Br)

According to PROCEDURE 1, SiO$_2$ was tested for stability versus [PBu$_4$]Br at T=250° C. for t=168 h. The mass change was less than 0.1% and no surface topology change and no haptic change could be observed. The color of the chemical changes slightly. SiO$_2$ is stated as stable with minor changes versus [PBu$_4$]Br up to at least 250° C.

Example 133—Stability of Titanium Grade 2 (TiG2) Versus Tetrabutylphosphonium Bromide ([PBu$_4$]Br)

According to PROCEDURE 1, TiG2 was tested for stability versus [PBu$_4$]Br at T=250° C. for t=168 h. Corrosion could be observed. TiG2 is stated as not stable versus [PBu$_4$]Br at 250° C.

Example 134—Stability of Hastelloy C-276 (C-276) Versus Tetrabutylphosphonium Bromide ([PBu$_4$]Br)

According to PROCEDURE 1, C-276 was tested for stability versus [PBu$_4$]Br at T=250° C. for t=168 h. Corrosion could be observed. C-276 is stated as not stable versus [PBu$_4$]Br at 250° C.

Example 135—Stability of Stainless Steel 1.4571 (1.4571) Versus Tetrabutylphosphonium Bromide ([PBu$_4$]Br)

According to PROCEDURE 1, 1.4571 was tested for stability versus [PBu$_4$]Br at T=250° C. for t=168 h. Corrosion could be observed. 1.4571 is stated as not stable versus [PBu$_4$]Br at 250° C.

Example 136—Stability of Aluminum (Al) Versus Tetrabutylphosphonium Bromide ([PBu$_4$]Br)

According to PROCEDURE 1, Al was tested for stability versus [PBu$_4$]Br at T=250° C. for t=168 h. Corrosion could be observed. Al is stated as not stable versus [PBu$_4$]Br at 250° C.

Example 137—Stability of Polytetrafluorethylene (PTFE) Versus Tetrabutylphosphonium Bromide ([PBu$_4$]Br)

According to PROCEDURE 1, PTFE was tested for stability versus [PBu$_4$]Br at T=250° C. for t=168 h. The mass change was less than 0.1% and no color change, no surface topology change and no haptic change could be observed. PTFE is stated as stable versus [PBu$_4$]Br up to at least 250° C.

Example 138—Stability of Perfluoroalkoxy Alkane (PFA) Versus Tetrabutylphosphonium Bromide ([PBu$_4$]Br)

According to PROCEDURE 1, PFA was tested for stability versus [PBu$_4$]Br at T=250° C. for t=168 h. The mass change was less than 0.1% and no color change, no surface topology change and no haptic change could be observed. PFA is stated as stable versus [PBu$_4$]Br up to at least 250° C.

Example 139—Stability of Perfluoroelastomer (FFKM) Versus Tetrabutylphosphonium Bromide ([PBu$_4$]Br)

According to PROCEDURE 1, FFKM was tested for stability versus [PBu$_4$]Br at T=250° C. for t=168 h. The mass increase was less than 10% and no color change could be observed. FFKM is stated as stable with minor changes versus [PBu$_4$]Br up to at least 250° C.

Example 140—Stability of Fluoroelastomer (FKM) Versus Tetrabutylphosphonium Bromide ([PBu$_4$]Br)

According to PROCEDURE 1, FKM was tested for stability versus [PBu$_4$]Br at T=250° C. for t=168 h. The mass increase was more than 10%. FKM is stated as not stable versus [PBu$_4$]Br at 250° C.

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making acrylic acid, acrylic acid derivatives, or mixtures thereof comprising contacting a feed stream comprising lactic acid, lactic acid derivatives, or mixtures thereof with a molten salt catalyst in a reactor at a temperature; wherein said molten salt catalyst comprises an ionic liquid (IL) and a Lewis acid that is soluble in the IL; and whereby acrylic acid, acrylic acid derivatives, or mixtures thereof are produced as a result of said contacting in said reactor; wherein said IL has a bromide (Br$^-$) anion and a phosphonium cation; wherein said contacting is performed at atmospheric pressure; wherein said contacting proceeds in the presence of a strip gas.

2. The method of claim 1 wherein said IL has an organic cation selected from the group consisting of imidazolium, pyridinium, pyrrolidinium, ammonium, phosphonium, their derivatives, and mixtures thereof.

3. The method of claim 1 wherein said lactic acid derivatives are selected from the group consisting of lactic acid with its carboxylic acid group protected, lactic acid with its hydroxyl group replaced by a better leaving group, lactic acid with both its carboxylic acid group protected and hydroxyl group replaced by a better leaving group, and mixtures thereof.

4. The method of claim 3 wherein said lactic acid derivatives are selected from the group consisting of lactide, 2-acetoxypropionic acid (2-APA), ethyl 2-trifluoroacetoxypropionate (ETFP), and 2-bromopropionic acid (2-BrPA).

5. The method of claim 1 wherein said IL is [PBu$_4$]Br; and wherein said acid is selected from the group consisting of CaBr$_2$, MgBr$_2$, AlBr$_3$, and mixtures thereof.

6. The method of claim 4 wherein said lactic acid derivative is ethyl 2-trifluoroacetoxypropionate (ETFP).

7. The method of claim 1 wherein said strip gas is selected from the group consisting of air, nitrogen, argon, carbon monoxide and mixtures thereof.

8. The method of claim 7 wherein said acrylic acid, acrylic acid derivatives, or mixtures thereof are produced with a yield of at least about 30 mol %.

9. A method of making acrylic acid comprising contacting a feed stream comprising 2-acetoxypropionic acid (2-APA) with a molten salt catalyst in a reactor at 220° C.; wherein said molten salt catalyst comprises [EtPPh$_3$]Br and HBr at a molar ratio of about 4 to 1 respectively; wherein said contacting proceeds under atmospheric pressure; and whereby acrylic acid is produced as a result of said contacting in said reactor with an acrylic acid yield of at least about 25 mol %; wherein said contacting proceeds in the presence of a strip gas.

* * * * *